United States Patent [19]
Dombroski et al.

[11] Patent Number: 6,133,286
[45] Date of Patent: Oct. 17, 2000

[54] TETRAHYDRONAPHTHALENE AND TETRAHYDROQUINOLINE COMPOUNDS, THEIR PREPARATION AND THEIR USE AS LEUKOTRIENE $B_4$ ($LTB_4$) ANTAGONISTS

[75] Inventors: Mark A. Dombroski; Kevin Koch; Anthony D. Piscopio, all of Groton, Conn.

[73] Assignee: Pfizer Inc., New York, N.Y.

[21] Appl. No.: 09/493,707

[22] Filed: Jan. 28, 2000

Related U.S. Application Data

[62] Division of application No. 08/809,728, filed as application No. PCT/IB95/00401, May 26, 1995, which is a continuation of application No. 08/322,876, Oct. 13, 1994, abandoned.

[51] Int. Cl.[7] ............... C07D 215/233; C07C 39/14; C07C 39/17; A61K 31/045
[52] U.S. Cl. ............... 514/312; 514/570; 546/153; 546/155; 562/492
[58] Field of Search ............... 514/312, 570; 546/153, 155; 562/492

[56] References Cited

FOREIGN PATENT DOCUMENTS

WO 93/15067  8/1993  WIPO.

*Primary Examiner*—Mukund J. Shah
*Assistant Examiner*—Deepak R. Rao
*Attorney, Agent, or Firm*—Peter C. Richardson; Paul H. Ginsburg; Jolene W. Appleman

[57] ABSTRACT

This invention relates to novel benzopyran and other benzo-fused leukotriene $B_4$ ($LTB_4$) antagonists and the pharmaceutically acceptable salts thereof, to pharmaceutical compositions containing such compounds or a pharmaceutically acceptable salt thereof, and to methods of using such compounds as $LTB_4$ antagonists. The compounds and the pharmaceutically acceptable salts of this invention inhibit the action of $LTB_4$ and are therefore useful in the treatment of $LTB_4$ induced illnesses such as inflammatory disorders including rheumatoid arthritis, osteoarthritis, inflammatory bowel disease, psoriasis and other skin disorders such as eczema, erythema, pruritus and acne, stroke and other forms of reperfusion injury, graft rejection, autoimmune diseases, asthma, and other conditions where marked neutrophil infiltration occurs.

13 Claims, No Drawings

6,133,286

TETRAHYDRONAPHTHALENE AND TETRAHYDROQUINOLINE COMPOUNDS, THEIR PREPARATION AND THEIR USE AS LEUKOTRIENE $B_4$ ($LTB_4$) ANTAGONISTS

CROSS REFERENCE TO RELATED APPLICATIONS

This application is a divisional of U.S. application Ser. No. 08/809,728 filed Apr. 9, 1997, which is the national stage of International Application No. PCT/IB95/00401, having an international filing date of May 26, 1995, designating, inter alia, the United States which is a continuation of U.S. application Ser. No. 08/322,876, filed Oct. 13, 1994, now abandoned.

BACKGROUND OF THE INVENTION

This invention relates to novel benzopyran and other benzo-fused leukotriene $B_4$ ($LTB_4$) antagonists, the pharmaceutically acceptable salts of said compounds, to pharmaceutical compositions containing such compounds, and to a method of using such compounds as $LTB_4$ antagonists.

The compounds of this invention inhibit the action of $LTB_4$ and are therefore useful in the treatment of $LTB_4$ induced illnesses such as inflammatory disorders including rheumatoid arthritis, osteoarthritis, inflammatory bowel disease, psoriasis and other skin disorders such as eczema, erythema, pruritus and acne, stroke and other forms of reperfusion injury, graft rejection, autoimmune diseases, asthma, and other conditions where marked neutrophil infiltration occurs.

Leukotriene $B_4$ antagonists are disclosed in European patent publications 276 064 and 292 977 which refer to diphenylethers, benzophenones, and other compounds containing two phenyl groups, and 7-(3-alkoxy-4-alkanoyl-phenoxy)alkoxy benzopyran derivatives, respectively.

SUMMARY OF THE INVENTION

The present invention is directed to novel benzopyran and other benzo-fused leukotriene $B_4$ ($LTB_4$) antagonist compounds, of the formula

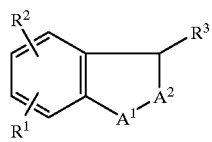

(I)

and the pharmaceutically acceptable salts thereof wherein
$A^1$ is O, $CH_2$, S, NH or $N(C_1-C_6)$alkyl;
$R^3$ is hydrogen or hydroxy;

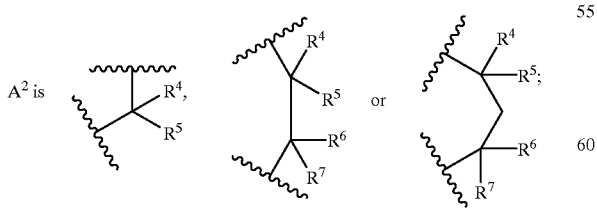

$R^4$ is hydrogen or hydroxy;
$R^5$ is selected from the group consisting of —$(CH_2)_n CHX^9X^{10}$, —$(CH_2)_n X^{10}$ and —$CH(OH)X^{10}$;

wherein
n is 0, 1, 2, or 3;
$X^9$ is hydrogen, $(C_1-C_6)$alkyl or optionally substituted phenyl;
wherein the optionally substituted phenyl is optionally substituted by one or two substituents independently selected from the group consisting of fluoro, chloro, $(C_1-C_6)$alkyl, $(C_1-C_6)$alkoxy, $(C_1-C_4)$perfluoroalkyl, $(C_1-C_4)$perfluoroalkoxy, $(C_1-C_6)$alkylthio, $(C_1-C_8)$alkylsulfinyl, phenylsulfinyl, $(C_1-C_6)$alkylsulfonyl and phenylsulfonyl;
$X^{10}$ is hydrogen, $(C_1-C_8)$alkyl, $(C_3-C_8)$cycloalkyl or one of the following optionally substituted rings: phenyl, thienyl, pyridyl, furyl, naphthyl, quinolyl, isoquinolyl, pyrimidinyl or pyrazinyl;
where the optionally substituted rings are optionally substituted by one or two substituents independently selected from the group consisting of fluoro, chloro, $(C_1-C_6)$alkyl, $(C_1-C_6)$alkoxy, $(C_1-C_4)$perfluoro-alkyl, $(C_1-C_4)$perfluoroalkoxy, $(C_1-C_6)$alkylthio, $(C_1-C_6)$alkylsulfinyl, phenylsulfinyl, $(C_1-C_6)$alkylsulfonyl, phenylsulfonyl and optionally substituted phenyl;
where the optionally substituted phenyl is optionally substituted by one or two substituents independently selected from the group consisting of fluoro, chloro, $(C_1-C_6)$alkyl, $(C_1-C_6)$alkoxy, $(C_1-C_4)$perfluoroalkyl, $(C_1-C_4)$perfluoroalkoxy, $(C_1-C_6)$alkylthio, $(C_1-C_6)$alkylsulfonyl, phenylsulfinyl, $(C_1-C_6)$alkylsulfonyl and phenylsulfonyl;
$R^6$ and $R^7$ are each independently hydrogen or $(C_1-C_4)$alkyl or $R^6$ and $R^7$ are taken together with the carbon atom to which they are attached and form a $(C_4-C_7)$cycloalkyl;
$R^1$ is selected from the group consisting of tetrazolyl, carboxy, cis or trans —$(CH_2)_m$—$CX^1$=$CX^2$—$CO_2H_1$—$(CH_2)_m CX^3X^4X^5$, —CO—$NG^1G^2$

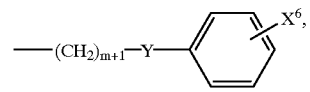

and a substituted five or six membered aromatic ring optionally having one or two heteroatoms where the heteroatoms are optionally independently selected from the group consisting of O, S and N;
wherein
m is 0, 1 or 2;
Y is O, $CH_2$, S, NH or $N(C_1-C_6)$alkyl;
$X^1$ and $X^2$ are each independently hydrogen or $(C_1-C_6)$alkyl;
$X^3$ and $X^4$ are each independently hydrogen or $(C_1-C_6)$alkyl or $X^3$ and $X^4$ are taken together with the carbon atom to which they are attached and form a $(C_3-C_7)$cycloalkyl;
$X^5$ is hydroxy, carboxy, tetrazolyl or —CO—$NG^3G^4$;
$X^6$ is carboxy, tetrazolyl, $CH_2OH$ or —CO—$NG^5G^5$;
$G^1$, $G^2$, $G^3$, $G^4$, $G^5$, and $G^6$ are each independently selected from the group consisting of hydrogen, $(C_1-C_6)$alkyl, $(C_1-C_4)$perfluoroalkyl, $(C_1-C_8)$alkylsulfinyl, phenylsulfinyl, $(C_1-C_6)$alkylsulfonyl, phenylsulfonyl, hydroxy, phenyl and $(Q^1)_a$-substituted phenyl;
where
a is 1 or 2; $Q^1$ for each occurrence is independently selected from fluoro, chloro, $(C_1-C_6)$- alkyl, $(C_1-C_6)$alkoxy, $(C_1-C_4)$perfluoroalkyl, $(C_1-C_4)$perfluoroalkoxy, $(C_1-C_6)$alkylthio, $(C_1-C_6)$alkylsulfinyl, phenylsulfinyl, $(C_1-C_6)$ alkylsulfonyl and phenylsulfonyl;

the substituted five or six membered aromatic ring is substituted by one substituent selected from the group consisting of carboxy, tetrazolyl, —CO—N(H)(SO$_2$—X$^7$), —N(H)(SO$_2$—X$^7$), —N(H)(CO—X$^7$), and —N(H)(CO—OX$^7$) and by one or two substituents each independently selected from the group consisting of fluoro, chloro, $(C_1-C_8)$alkyl, $(C_1-C_6)$alkoxy, $(C_1-C_4)$perfluoroalkyl, $(C_1-C_4)$perfluoroalkoxy, $(C-C_6)$alkylthio, $(C_1-C_6)$alkylsulfinyl, phenylsulfinyl, $(C_1-C_6)$alkylsulfonyl, and phenylsulfonyl;

wherein X$^7$ is hydrogen, —CH$_2$F, —CHF$_2$, —CF$_3$, $(C_1-C_6)$alkyl, $(C_3-C_8)$cycloalkyl or one of the following optionally substituted rings: phenyl, thienyl, pyridyl, furyl, naphthyl, quinolyl, isoquinolyl, pyrimidinyl or pyrazinyl;

where the optionally substituted rings are optionally substituted with one or two substituents independently selected from the group consisting of fluoro, chloro, $(C_1-C_8)$alkyl, $(C_1-C_6)$alkoxy, $(C_1-C_4)$perfluoroalkyl, $(C_1-C_4)$perfluoroalkoxy, $(C_1-C_6)$alkylthio, $(C_1-C_6)$alkylsulfinyl, phenylsulfinyl, $(C_1-C_6)$alkylsulfonyl, phenylsulfonyl and optionally substituted phenyl;

where the optionally substituted phenyl is optionally substituted with one or two substituents independently selected from the group consisting of fluoro, chloro, $(C_1-C_6)$alkyl, $(C_1-C_6)$ alkoxy, $(C_1-C_4)$perfluoroalkyl, $(C_1-C_4)$ perfluoroalkoxy, $(C_1-C_6)$alkylthio, $(C_1-C_6)$ alkylsulfinyl, phenylsulfonyl, $(C_1-C_6)$ alkylsulfonyl and phenylsulfonyl;

R$^2$ is hydrogen, fluoro, chloro, $(C_1-C_6)$alkyl, $(C_1-C_6)$ alkoxy, $(C_1-C_4)$perfluoroalkyl, $(C_1-C_4)$ perfluoroalkoxy, $(C_1-C_6)$alkylthio, $(C_1-C_6)$ alkylsulfinyl, phenylsulfinyl, $(C_1-C_6)$alkylsulfonyl or phenyisulfonyl; with the provisos that:

G$^1$ and G$^2$ are not both hydroxy at the same time;
G$^3$ and G$^4$ are not both hydroxy at the same time;
G$^5$ and G$^6$ are not both hydroxy at the same time; and when R$^3$ is hydroxy and R$^4$ is hydrogen then R$^5$ is —CH(OH)X$^{10}$.

A preferred group of compounds are those compounds of the formula I or a pharmaceutically acceptable salt thereof wherein R$^3$ is hydroxy; A$^2$ is

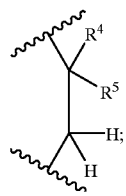

and R$^1$, R$^2$, A$^1$, R$^4$ and R$^5$ are as defined above for formula I.

A more preferred group of compounds are those compounds of the formula I or a pharmaceutically acceptable salt thereof wherein R$^3$ is hydroxy; A$^1$ is O or CH$_2$; A$^2$ is

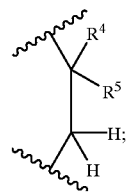

and R$^1$, R$^2$, R$^4$ and R$^5$ are as defined above for formula I.

A yet more preferred group of compounds are those compounds of the formula I or a pharmaceutically acceptable salt thereof wherein R$^3$ is hydroxy; A$^1$ is O or CH$_2$; A$^2$ is

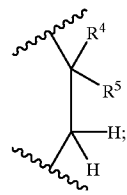

R$^1$ is —(CH$_2$)$_m$CX$^3$X$^4$X$^5$ or a substituted five or six membered aromatic ring substituted with one substituent selected from the group consisting of carboxy, tetrazolyl, —CO—N(H)(SO$_2$—X$^7$), —N(H)(SO$_2$—X$^7$), —N(H) (CO—X$^7$), and —N(H) (CO—OX$^7$) and with one or two substituents each independently selected from the group consisting of fluoro, chloro, $(C_1-C_6)$alkyl, $(C_1-C_6)$alkoxy, $(C_1-C_4)$perfluoroalkyl, $(C_1-C_4)$perfluoroalkoxy, $(C_1-C_6)$alkylthio, $(C_1-C_6)$ alkylsulfinyl, phenylsulfinyl, $(C_1-C_6)$alkylsulfonyl, and phenylsulfonyl; and m, X$^3$, X$^4$, X$^5$, X$^7$, R$^2$, R$^4$ and R$^5$ are as defined above for formula I.

An even more preferred group of compounds are those compounds of the formula I or a pharmaceutically acceptable salt thereof wherein R$^3$ is hydroxy; A$^1$ is O or CH$_2$; A$^2$ is

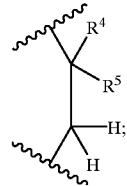

R$^1$ is a substituted phenyl substituted with one substituent selected from the group consisting of carboxy, —N(H)(SO$_2$—X$^7$), —N(H)(CO—X$^7$), and —N(H)(CO—OX$^7$) and with one or two substituents each independently selected from the group consisting of fluoro, chloro, $(C_1-C_6)$alkyl, $(C_1-C_8)$alkoxy, $(C_1-C_4)$perfluoroalkyl, $(C_1-C_4)$perfluoroalkoxy, $(C_1-C_6)$alkylthio, $(C_1-C_6)$alkylsulfinyl, phenylsulfinyl, $(C_1-C_6)$alkylsulfonyl, and phenylsulfonyl; and X$^7$, R$^2$, R$^4$ and R$_5$ are as defined above for formula I.

A most preferred group of compounds are those compounds of the formula I or pharmaceutically acceptable salt thereof wherein R$^3$ is hydroxy; A$^1$ is O or CH$_2$; A$^2$ is

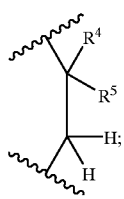

R[1] is a substituted phenyl substituted with one substituent selected from the group consisting of carboxy, —N(H)(SO$_2$—X[7]), —N(H)(CO—X[7]), and —N(H)(CO—OX[7]) and with one or two substituents each independently selected from the group consisting of fluoro, chloro, (C$_1$–C$_6$)alkyl, (C$_1$–C$_6$)alkoxy, (C$_1$–C$_4$)perfluoroalkyl, (C$_1$–C$_4$)perfluoroalkoxy, (C$_1$–C$_6$)alkylthio, (C$_1$–C$_6$)alkylsulfinyl, phenylsulfinyl, (C$_1$–C$_6$)alkylsulfonyl, and phenylsulfonyl; R[4] is hydroxy and the R[3] hydroxy is either cis or trans with the R[4] hydroxy; and X[7], R[2] and R[5] are as defined above for formula I. Of the immediately foregoing group of most preferred compounds are an even more preferred group of compounds wherein the R[3] and R[4] hydroxy groups are cis to each other.

Yet another most preferred group of compounds are those compounds of the formula I or a pharmaceutically acceptable salt thereof wherein R[3] is hydroxy; R[4] is hydroxy; A[1] is O or CH$_2$; A[2] is

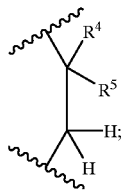

R[1] is a substituted phenyl substituted with one substituent selected from the group consisting of carboxy and —N(H)(SO$_2$—X[7]), and with one or two substituents each independently selected from the group consisting of fluoro, chloro, (C$_1$–C$_6$)alkyl, (C$_1$–C$_6$)alkoxy, (C$_1$–C$_4$)perfluoroalkyl, (C$_1$–C$_4$)perfluoroalkoxy, (C$_1$–C$_6$)alkylthio, (C$_1$–C$_6$)alkylsulfinyl, phenylsulfinyl, (C$_1$–C$_6$)alkylsulfonyl, and phenylsulfonyl; the R[3] hydroxy and R[4] hydroxy are cis to each other; R[5] is —(CH$_2$)$_n$CHX[9]X[10], where X[9] is hydrogen and X[10] is one of the optionally substituted rings as defined above for formula I; and n, X[7] and R[2] are as defined above for formula I. A preferred group of compounds within the immediately foregoing group of compounds are those compounds wherein n is 1; and X[10] is phenyl substituted at the para position with phenyl. And the following group of compounds are the most preferred group of compounds thereof wherein R[1] is a substituted phenyl substituted with one substituent selected from the group consisting of carboxy and —N(H)(SO$_2$—X[7]), and with one or two substituents each independently selected from the group consisting of fluoro, chloro and (C$_1$–C$_4$)perfluoroalkyl.

The present invention also relates to a pharmaceutical composition for the treatment of LTB$_4$ induced illnesses which comprises an effective amount of a compound of the formula I or a pharmaceutically acceptable salt thereof as defined above or a pharmaceutically-acceptable salt thereof and a pharmaceutically acceptable carrier or diluent. The invention further relates to a pharmaceutical composition for the treatment of eczema, erythema, pruritus, acne, stroke, graft rejection, autoimmune diseases, and asthma comprising an amount of a compound of the formula I as defined above or a pharmaceutically-acceptable salt thereof which is sufficient for the treatment of said diseases, and a pharmaceutically acceptable carrier or diluent. Preferred compositions are those wherein the compound of formula I is a preferred compound.

This invention further comprises a method for the receptor binding inhibition, functional activity inhibition and in vivo inhibition of LTB$_4$ by administering to a subject in need of such inhibition a compound of formula I as defined above or a pharmaceutically-acceptable salt thereof. The invention includes a method for the treatment of inflammatory disorders, eczema, erythema, pruritus, acne, stroke, graft rejection, autoimmune diseases, and asthma by administering to a subject in need of such treatment a compound of formula I as defined above or a pharmaceutically-acceptable salt thereof. Preferred methods according to the invention are those wherein the compound of formula I is a preferred compound or a pharmaceutically-acceptable salt thereof.

This invention is also directed to an intermediate compound of formula 1A

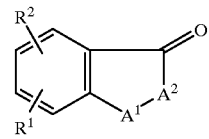

(1A)

wherein A[1] is O, CH$_2$, S, NH or N(C$_1$–C$_6$)alkyl;
A[2] is

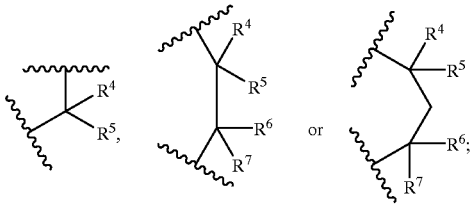

R[4] is hydrogen or hydroxy;
R[5] is selected from the group consisting of —(CH$_2$)$_n$CHX[9]X[10], —(CH$_2$)$_n$X[10] and —CH(OH)X[10];
wherein
n is 0, 1, 2, or 3;
X[9] is hydrogen, (C$_1$–C$_6$)alkyl or optionally substituted phenyl;
wherein the optionally substituted phenyl is optionally substituted by one or two substituents independently selected from the group consisting of fluoro, chloro, (C$_1$–C$_6$)alkyl, (C$_1$–C$_6$)alkoxy, (C$_1$–C$_4$)perfluoroalkyl, (C$_1$–C$_4$)perfluoroalkoxy, (C$_1$–C$_6$)alkylthio, (C$_1$–C$_6$)alkylsulfinyl, phenylsulfinyl, (C$_1$–C$_6$)alkylsulfonyl and phenylsulfonyl;
X[10] is hydrogen, (C$_1$–C$_6$)alkyl, (C$_3$–C$_8$)cycloalkyl or one of the following optionally substituted rings: phenyl, thienyl, pyridyl, furyl, naphthyl, quinolyl, isoquinolyl, pyrimidinyl or pyrazinyl;
where the optionally substituted rings are optionally substituted by one or two substituents independently selected from the group consisting of fluoro, chloro, $(C_1-C_6)$alkyl, $(C_1-C_6)$alkoxy, $(C_1-C_4)$perfluoro-alkyl, $(C_1-C_4)$perfluoroalkoxy, $(C_1-C_6)$alkylthio, $(C_1-C_6)$alkylsulfinyl, phenylsulfinyl, $(C_1-C_6)$alkylsulfonyl, phenylsulfonyl and optionally substituted phenyl;

where the optionally substituted phenyl is optionally substituted by one or two substituents independently selected from the group consisting of fluoro, chloro, $(C_1-C_6)$alkyl, $(C_1-C_6)$alkoxy, $(C_1-C_4)$perfluoroalkyl, $(C_1-C_4)$perfluoroalkoxy, $(C_1-C_6)$alkylthio, $(C_1-C_6)$alkylsulfinyl, phenylsulfinyl, $(C_1-C_6)$alkylsulfonyl and phenylsulfonyl;

$R^6$ and $R^7$ are each independently hydrogen or $(C_1-C_4)$ alkyl or $R^6$ and $R^7$ are taken together with the carbon atom to which they are attached and form a $(C_4-C_7)$ cycloalkyl;

$R^1$ is selected from the group consisting of tetrazolyl, carboxy, cis or trans $—(CH_2)_m—CX^1=CX^2—CO_2H$, $—(CH_2)_mCX^3X^4X^6$, $—CO—NG^1G^2$,

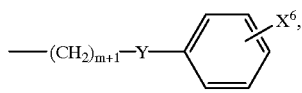

and a substituted five or six membered aromatic ring optionally having one or two heteroatoms where the heteroatoms are optionally independently selected from the group consisting of O, S and N;
wherein
m is 0, 1 or 2;
Y is O, $CH_2$, S, NH or $N(C_1-C_6)$alkyl;
$X^1$ and $X^2$ are each independently hydrogen or $(C_1-C_6)$ alkyl;
$X^3$ and $X^4$ are each independently hydrogen or $(C_1-C_6)$ alkyl or $X^3$ and $X^4$ are taken together with the carbon atom to which they are attached and form a $(C_3-C_7)$ cycloalkyl;
$X^5$ is hydroxy, carboxy, tetrazolyl or $—CO—NG^3G^4$;
$X^6$ is carboxy, tetrazolyl, $CH_2OH$ or $—CO—NG^5G^6$;
$G^1$, $G^2$, $G^3$, $G^4$, $G^5$, and $G^6$ are each independently selected from the group consisting of hydrogen, $(C_1-C_6)$alkyl, $(C_1-C_4)$perfluoroalkyl, $(C_1-C_6)$ alkylsulfinyl, phenylsulfinyl, $(C_1-C_6)$ alkylsulfonyl, phenylsulfonyl, hydroxy, phenyl and $(Q^1)_a$-substituted phenyl;
where a is 1 or 2;
$Q^1$ for each occurrence is independently selected from fluoro, chloro, $(C^1-C_6)$-alkyl, $(C_1-C_6)$ alkoxy, $(C_1-C_4)$perfluoroalkyl, $(C_1-C_4)$ perfluoroalkoxy, $(C_1-C_6)$alkylthio, $(C_1-C_5)$ alkylsulfinyl, phenylsulfinyl, $(C_1-C_6)$ alkylsulfonyl and phenylsulfonyl;
the substituted five or six membered aromatic ring is substituted by one substituent selected from the group consisting of carboxy, tetrazolyl, $—CO—N(H)(SO_2—X^7)$, $—N(H)(SO_2—X^7)$, $—N(H)(CO—X^7)$, and $—N(H)(CO—OX^7)$ and by one or two substituents each independently selected from the group consisting of fluoro, chloro, $(C_1-C_6)$alkyl, $(C_1-C_6)$alkoxy, $(C_1-C_4)$perfluoroalkyl, $(C_1-C_4)$perfluoroalkoxy, $(C_1-C_6)$alkylthio, $(C_1-C_6)$alkylsulfinyl, phenylsulfinyl, $(C_1-C_6)$alkylsulfonyl, and phenylsulfonyl;
wherein $X^7$ is hydrogen, $—CH_2F$, $—CHF_2$, $—CF_3$, $(C_1-C_6)$alkyl, $(C_3-C_8)$cycloalkyl or one of the following optionally substituted rings: phenyl, thienyl, pyridyl, furyl, naphthyl, quinolyl, isoquinolyl, pyrimidinyl or pyrazinyl;

where the optionally substituted rings are optionally substituted by one or two substituents independently selected from the group consisting of fluoro, chloro, $(C_1-C_6)$alkyl, $(C_1-C_6)$alkoxy, $(C_1-C_4)$perfluoroalkyl, $(C_1-C_4)$perfluoroalkoxy, $(C_1-C_6)$alkylthio, $(C_1-C_6)$alkylsulfinyl, phenylsulfinyl, $(C_1-C_6)$alkylsulfonyl, phenylsulfonyl and optionally substituted phenyl;

where the optionally substituted phenyl is optionally substituted by one or two substituents independently selected from the group consisting of fluoro, chloro, $(C_1-C_6)$alkyl, $(C_1-C_6)$ alkoxy, $(C_1-C_4)$perfluoroalkyl, $(C_1-C_4)$ perfluoroalkoxy, $(C_1-C_6)$alkylthio, $(C_1-C_6)$ alkylsulfinyl, phenylsulfonyl, $(C_1-C_6)$ alkylsulfonyl and phenylsulfonyl;

$R^2$ is hydrogen, fluoro, chloro, $(C_1-C_6)$alkyl, $(C_1-C_6)$ alkoxy, $(C_1-C_4)$perfluoroalkyl, $(C_1-C_4)$ perfluoroalkoxy, $(C_1-C_6)$alkylthio, $(C_1-C_6)$ alkylsulfinyl, phenylsulfinyl, $(C_1-C_6)$alkylsulfonyl or phenylsulfonyl;

with the provisos that:
$G^1$ and $G^2$ are not both hydroxy at the same time;
$G^3$ and $G^4$ are not both hydroxy at the same time; and
$G^5$ and $G^6$ are not both hydroxy at the same time.

DETAILED DESCRIPTION OF THE INVENTION

The term "$C_1-C_6$ alkyl" whenever used in the disclosure herein denotes saturated monovalent straight or branched aliphatic hydrocarbon radicals having one to six carbon atoms, such as methyl, ethyl, propyl, t-butyl, hexyl, etc. Similarly, the terms $C_3-C_7$ cycloalkyl and $C_3-C_8$ cycloalkyl denote cycloalkyl groups having from three to seven or eight carbon atoms, respectively, such as cyclopropyl, cyclohexyl, cyclooctyl, etc.

When $A^1$ is oxygen and $A^2$ is

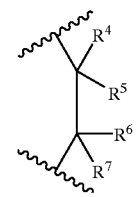

in a compound of formula I, the compound may be described either as a 3,4-dihydrobenzopyran or a chromane.

The compounds of the invention when $R^3$ is OH have two asymmetric carbon atoms indicated by asterisks in the following formula:

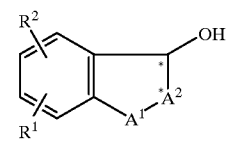

The stereoisomers may be designated with reference to R and S rotation in accordance with standard nomenclature. When reference is made herein to S,R or R,S a single enantiomerically pure compound is meant, whereas S*, R* and R*, S* denote a racemic mixture. The invention includes the racemic mixtures and optical isomers of formula I.

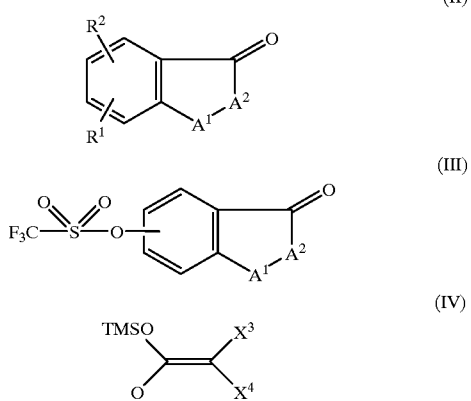

According to a specific method of the invention, compounds of above formula II, which are intermediate compounds of formula I, wherein $R^1$ is —$(CH_2)_m X^3 X^4 X^5$, wherein m is 0 and $X^5$ is carboxy or the esters thereof, are prepared by reacting compounds of above formulae III and IV to form a compound of the formula V (not shown) followed by reduction to form the compound of formula I.

The reaction of compounds IIII and IV is generally conducted in a solvent. Suitable solvents are ether solvents such as tetrahydrofuran, diethyl ether, ethylene glycol dimethyl ether and 1,4-dioxane, dipolar aprotic solvents such as dimethylformamide, N,N-dimethylacetamide, acetonitrile, dimethyl sulfoxide, hexamethylphosphoramide, N,N-dimethylpropylene urea, non-polar aromatic solvents such as xylene, benzene, chlorobenzene and toluene, and halogenated solvents such as methylene chloride, chloroform and dichloroethane. Specific suitable solvents are xylene, or a mixture of equal volumes of ethylene glycol dimethylether and dimethyl formamide. The reaction temperature ranges from −78° C. to 200° C. depending on the boiling point of the solvent used and usually ranges from about 80° to about 150° C.

The reaction may be carried out in the presence of a Lewis acid such as zinc chloride, aluminum chloride, magnesium bromide, tin chloride and titanium chloride. When present, the amount of Lewis acid ranges from about 0.05 to about 2 equivalents per mole of compound III.

The reaction is generally carried out with a palladium catalyst. Suitable palladium catalysts are tetrakistriphenylphosphine palladium, bis-benzonitrile palladium chloride, allyl palladium chloride dimer, palladium chloride, palladium acetate, palladium on carbon, and bisacetonitrile palladium chloride. A specific catalyst comprises 5% by weight allyl palladium chloride dimer or 5% by weight bisbenzonitrile palladium chloride. Generally, about 0.001 equivalent to one equivalent of catalyst per mole of substrate is used.

The reaction is generally carried out in the presence of a phosphine ligand such as triphenylphosphine, tri-o-tolylphosphine or tri-2-furylphosphine in an amount of about 0.1 to about 5, preferably 1 to 2, molar equivalents per mole of substrate used.

The reduction of the compound of the formula V is carried out in a conventional manner with sodium borohydride in an alcohol solvent at ambient temperature to form the compound of formula I after saponification.

The compounds of formula III wherein $R^5$ is —$(CH_2)_n CHX^9 X^{10}$ or —$(CH_2)_n X^{10}$ may be prepared as follows.

The compound of formula VI

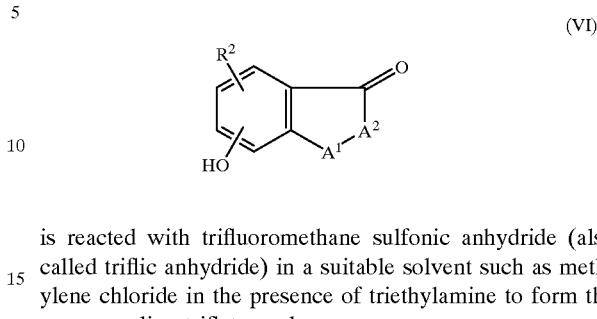

is reacted with trifluoromethane sulfonic anhydride (also called triflic anhydride) in a suitable solvent such as methylene chloride in the presence of triethylamine to form the corresponding triflate analog.

The group $R^5$ when defined as —$(CH_2)_n CHX^9 X^{10}$ or —$(CH_2)_n X^{10}$, wherein n, $X^9$ and $X^{10}$ are as defined above for formula I, may be introduced into the triflate analog by a two step procedure comprising reacting with an aldehyde of the formula $X^9 X^{10} CH(CH_2)_{q-1} CHO$ or $X^{10}(CH_2)_{q-1} CHO$ to form the corresponding alkene analog wherein $R^5$ is =$CH(CH_2)_{q-1} CHX^9 X^{10}$ or =$CH(CH_2)_{q-1} X^{10}$, wherein q is 1, 2, 3 or 4, respectively, and then hydrogenating. The reaction with the aldehyde is conducted in the presence of a pyrrolidine catalyst or with hydrochloric acid catalyst in acetic acid. The hydrogenation is carried out with hydrogen and a palladium catalyst in a conventional manner.

The compounds of formula VI are generally commercially available. If not, they may be obtained by methods well known to those skilled in the art. For instance, the compounds of formula VI wherein $A^1$ is oxygen and $A^2$ is

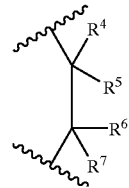

may be obtained from $R^2$-substituted 2',4'-dihydroxy-3-chloropropiophenone (hereafter compound 1) by cyclization with sodium hydroxide. Compound 1 may be prepared from $R^2$-substituted resorcinol and 3-chloropropionic acid in the presence of an acid, preferably trifluoromethane sulfonic acid. The compounds of formula VI wherein $A^1$ is sulphur and $A^2$ is

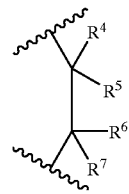

may similarly be obtained from $R^2$-substituted 4' or 5'-hydroxy-2'-sulfhydryl-3-chloro-propiophenone which, in turn, may be obtained from $R^2$-substituted 3-hydroxythiophenol.

The compounds of formula VI wherein $A^2$ is

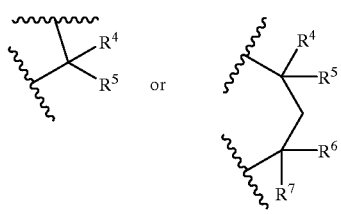

and $A^1$ is O or S may similarly be obtained by reaction of $R^2$-substituted resorcinol or 3-hydroxythiophenol, respectively, and 4-chlorobutyric acid (and its derivatives), and cyclization with sodium hydroxide.

Compounds of formula I wherein $R^1$ is —$(CH_2)_m$—CX=$CX^2$—$CO_2H$ may be synthesized by the reaction of the compound of formula III with $(CH_3)_3SnSn(CH_3)_3$ and a palladium catalyst such as tetrakistriphenylphosphine palladium $(Pd(PPh_3)_4)$ in the presence of a phosphine ligand, as described above for the reaction of compounds of the formulas III and IV to yield the corresponding trimethyltin analog. The trimethyltin analog is converted to an ester-protected compound of the formula $Z^1O_2CX^2C$=$CX^1$-$(CH_2)_mZ^2$ wherein $Z^1$ is alkyl or cycloalkyl and $Z^2$ is iodo, bromo or $CF_3SO_3$. The coupling reaction proceeds in the presence of a palladium catalyst, such as bistriphenyl phosphine palladium chloride, as described above. The ketone esters are first reduced to the corresponding hydroxyl compounds and then hydrolyzed to the corresponding acid of formula I. The reduction proceeds with sodium borohydride. Generally, the reduction is carried out in a solvent. Suitable solvents are lower alcohols having one to six carbon atoms, mixtures of lower alcohols with organic solvents such as tetrahydrofuran or dioxane, and mixtures of water-miscible lower alcohols or other water-miscible organic solvents with water. The solvent is preferably a lower alcohol such as methanol or ethanol. The reaction temperature generally ranges from about −78° C. to about 100° C., and usually from about 0° C. to about 25° C.

The reduction step results in a stereoisomeric mixture of the ester compounds of formula I having the following structures:

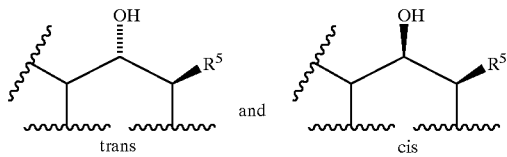

These cis and trans isomers may be separated by conventional column chromatography.

Resolution of the enantiomeric mixture resulting after separation of the cis and trans isomers may be accomplished by methods known in the art. In one method, a compound of the formula I wherein $R^1$ contains a carboxyl group (COOH) is reacted with a chiral base such as d-ephedrine in a polar solvent such as ether to form diastereomeric salts which are separated and then converted into optically pure acids by treatment with an acid such as aqueous or methanolic hydrogen chloride. In another method, a compound of the formula I wherein $R^1$ contains a carboxylic acid ester group is reacted with an optically active acid such as R-mandelic acid or N-t-butoxycarbonyl-D-tryptophan to form diastereomeric esters with the hydroxyl group which after separation are converted into optically pure acids by treatment with a base such as sodium hydroxide in methanol or ethanol. Removal of the resolving ester group and hydrolysis of the carboxylic acid ester group in $R^1$ is conveniently carried out with aqueous base such as an alkali metal hydroxide, e.g. sodium hydroxide, at temperatures ranging from about room temperature to the reflux or boiling temperature of the solvent or solvent mixture used. The reaction may be conducted in the presence of a co-solvent such as methanol, ethanol or tetrahydrofuran.

The compound of formula I wherein $R^1$ is carboxy and $R^2$ is hydrogen may be prepared from the intermediate compound of the formula III by first replacing the $CF_3SO_3$— group with methoxycarbonyl, and then hydrolyzing. The replacement reaction proceeds with carbon monoxide in the presence of palladium acetate, 1,1'-bis(diphenylphosphine) ferrocene (DPPF), methanol and triethylamine. The hydrolysis is as previously described.

The compounds of formula I wherein $R^1$ is —$(CH_2)_mCX^3X^4X^5$, where m, $X^3$, $X^4$ and $X^5$ are as defined above for formula I, will be designated hereafter as compounds of the formula XXI (not shown). Although the following chemistry describes the preparation of compounds of formula XVI, wherein $R^1$ is —$(CH_2)_mCX^3X^4CO_2C_2H_5$, it is understood that the same chemistry applies to compounds of formula XVI having a different $R^1$, as defined with reference to formula I, which is inert under the reaction conditions specified below.

Compounds of formula XXI where $X^5$ is tetrazolyl may be prepared from compounds of the formula XVI

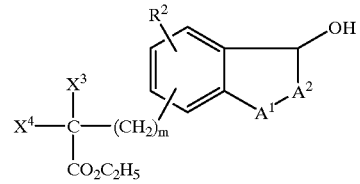

XVI

According to this method, a compound XVI is first reacted with t-butyldimethylsilylchloride in the presence of imidazole and dimethylformamide to protect the hydroxyl group as known in the art. The protected compound is reacted with ammonia and triethylaluminum in xylene to replace the —$CO_2C_2H_5$ group by cyano. The cyano group is replaced by trimethylstannyl-tetrazolyl by reaction with trimethylstannylazide in toluene. Conversion to the tetrazolyl and removal of the silyl protecting group is accomplished by reaction with tetrabutylammonium fluoride in tetrahydrofuran.

The starting material of formula XVI is identical to the compound of above formula II wherein $R^1$ is —$(CH_2)_mCX^3X^4X^5$ where $X^5$ is a carboxy ethyl ester, and m is 0. Preparation of this starting material is described above.

SCHEME I

-continued

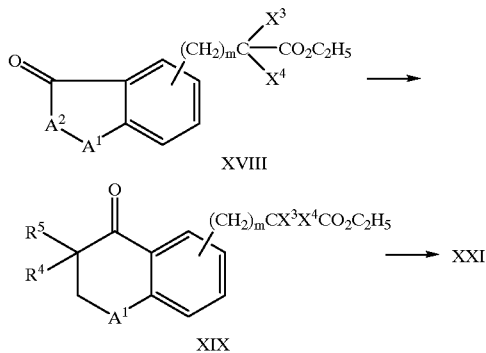

The compound of formula XVII is converted by subsequent reactions with (1) acrylonitrile, (2) hydrolysis with concentrated hydrochloride, and (3) cyclization with polyphosphoric acid to form the compound of formula XVIII. Introduction of group $R^5$ to form the compound of formula XIX is as described for compounds of formula VI. The hydrogenation and hydrolysis of the compound of formula XIX is as described hereinabove.

The compound of formula XVII may be prepared from 3-hydroxyphenyl acetic acid by introduction of groups $X^3$ and $X^4$ by known methods.

The starting material XVI when m is 0, 1 or 2, $A^2$ is

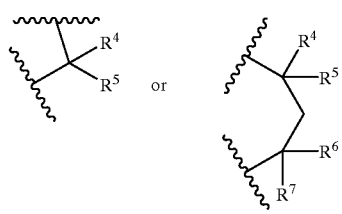

and $A^1$ is O, S, NH, or N($C_1$–$C_6$)alkyl may be prepared by reacting the compound of formula XVII with $BrCH_2CN$ or $BrCH_2CH_2CH_2CN$ in step (1) of Scheme I and converting further as described with reference to Scheme I.

The starting material XVI wherein $A^1$ is $CH_2$, m is 0, 1 or 2, and $A^2$ is

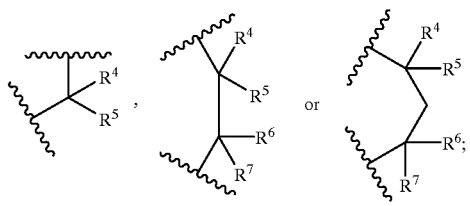

where $R^4$, $R^5$, $R^6$ and $R^7$ are as defined above for formula I may be prepared as described below.

A benzene substituted with —$(CH_2)_m$—$CX^3X^4CO_2C_2H_5$ is reacted with a mono acid chloride mono ester of malonic, succinic or glutaric acid in the presence of a Friedel Crafts catalyst such as aluminum chloride. The resulting ketone is converted to the corresponding propylene dithiol with propylene dithiol and boron trifluoride catalyst. The formed compound is reduced with Raney nickel, and then saponified. The ring is formed with polyphosphoric acid to produce the bicyclic compound XIX. Introduction of group $R^5$ is as described hereinabove.

Compounds of formula XXI wherein $X^5$ is $CO_2H$ may be prepared by saponification of a compound of the formula I wherein $R^1$ is —$(CH_2)_mCX^3X^4CO_2CH_3$ the preparation of which is described above.

Compounds of formula XXI wherein $X^5$ is OH, m is 0, 1 or 2, and $X^3$ and $X^4$ are each hydrogen may be prepared by conventional lithium aluminum hydride hydrogenation of a compound of the formula I wherein $R^1$ is —$(CH_2)_mCO_2CH_3$, wherein m is 0, 1 or 2.

Compounds of formula XXI wherein $X^5$ is OH, m is 0, 1 or 2, and $X^3$ and $X^4$ are each alkyl may be prepared by reacting the corresponding compounds wherein $X^3$ and $X^4$ are hydrogen with one equivalent of a Grignard reagent containing group $X^3$, e.g. $X^3MgCl$, followed by one equivalent of a Grignard reagent containing group $X^4$, e.g. $X^4MgCl$.

Compounds of formula XXI wherein $X^5$ is OH, m is 0, 1 or 2, and $X^3$ and $X^4$ are taken together to form $C_3$–$C_7$ cycloalkyl are similarly prepared by reacting the corresponding compounds wherein $X^3$ and $X^4$ are hydrogen with a Grignard reagent derived from a $C_3$–$C_7$ dihalo alkane, e.g. $ClMg(C_3$–$C_7$ alkanyl)$MgCl$.

The compounds of formula I wherein $R^1$ is

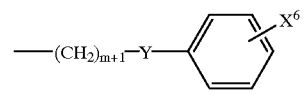

where $X^6$ is carboxy, tetrazolyl, —$CONG^5G^6$ or $CH_2OH$; Y is O, S, NH or NH($C_1$–$C_6$ alkyl); and m is 0, 1 or 2, may be prepared by reacting a compound of the formula

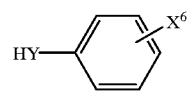

with a triflate compound of the formula I wherein $R^1$ is $CF_3SO_3CH_2(CH_2)_m$— in the presence of a base such as triethylamine or sodium hydride in a reaction inert solvent.

The triflates may be prepared by reacting triflic anhydride with the compound of formula XXI wherein m is 0, 1 or 2; $X^3$ and $X^4$ are hydrogen; and $X^5$ is hydroxyl, the synthesis of which is described above.

The compounds of formula I wherein $R^1$ is —$CONG^1G^2$ may be prepared from the corresponding compound wherein $R^1$ is carboxy by reaction with an amine of the formula $NHG^1G^2$.

According to a specific method of the invention, intermediate compounds of above formula II wherein $R^1$ is $CF_3$—$SO_2$—O—, are prepared by reacting a compound of the formula III as defined above with a compound of the formula

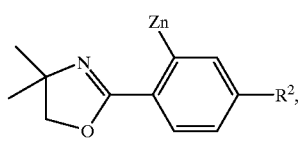

(1B)

wherein $R^2$ is as defined for formula I. This reaction generally proceeds in a solvent such as an ether solvent, e.g., tetrahydrofuran, diethyl ether, ethylene glycol dimethyl ether, 1,4-dioxane, and, preferably, tetrahydrofuran. The reaction is in the presence of a catalytic amount of a catalyst, particularly a palladium catalyst which is any palladium source which provides palladium (Pd°) under the reaction conditions, for instance tetrakistriphenylphosphine palladium. The reaction is usually carried out at or about the reflux temperature of the solvent used, preferably at about 78° C. The reaction time is generally from about 1 to 24 hours, e.g., about 3 hours.

The compounds of the formula 1 B are prepared in situ from a compound of the formula

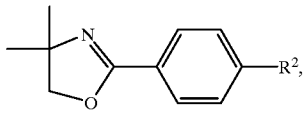

(1C)

where $R^2$ is as defined above for formula I, by reaction thereof with n-butyllithium or sec-butyllithium in hexanes at low temperatures of about −78° C., and then with $ZnCl_2$ or $ZnBr_2$, generally at about 0° C. to about 78° C. for about one to four hours.

Ketones of the formula II wherein $A^1$, $A^2$, $R^1$ and $R^2$ are as defined with reference to formula I may be reduced to the corresponding hydroxyl compounds of formula I by reaction with sodium borohydride. Generally, the reduction is carried out in a solvent. Suitable solvents are lower alcohols having one to six carbon atoms, mixtures of lower alcohols with organic solvents such as tetrahydrofuran or dioxane, and mixtures of water-miscible lower alcohols or other water-miscible organic solvents with water. The solvent is preferably a lower alcohol such as methanol or ethanol. The reaction temperature generally ranges from about −78° C. to about 100° C., and usually from about 0° C. to about 25° C.

SCHEME II

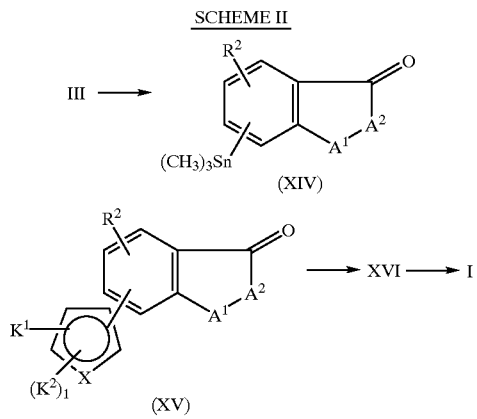

The compound of formula XIV is formed by reaction of the compound of formula III with $(CH_3)_3SnSn(CH_3)_3$ and a palladium catalyst such as tetrakistriphenylphosphine palladium ($Pd(PPh_3)_4$), or bis-benzonitrile palladium chloride, in the presence of a phosphine ligand, such as triphenyl phosphine, in an amount of about 0.1 to about 5 molar equivalents per mole of substrate used. The compound of formula XIV is converted to a compound of formula XV by reaction with an ester-protected compound of the formula

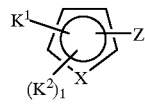

wherein X is C, CH, N, O or S; $K^1$ is carboxy protected as an ester, tetrazolyl, —CO—N(H)($SO_2$—$X^7$), —N(H)($SO_2$—$X^7$), —N(H)(CO—$X^7$) or —N(H)(CO—$OX^7$) (this group is prepared as the acid before being converted to the ester); $K^2$ is independently F, Cl, ($C_1$-$C_6$)alkyl, ($C_1$-$C_6$)alkoxy, ($C_1$-$C_4$)perfluoroalkyl, ($C_1$-$C_4$)perfluoroalkoxy, ($C_1$-$C_6$)alkylthio, ($C_1$-$C_6$)alkylsulfinyl, phenylsulfonyl, ($C_1$-$C_6$)alkylsulfonyl or phenylsulfonyl, l is 1 or 2 and Z is iodo, bromo or $CF_3SO_3$. The coupling reaction proceeds in the presence of a palladium catalyst, such as tetrakistriphenylphosphine palladium or bis-triphenylphosphine palladium chloride.

The ketone esters of the formula XV are first reduced to the corresponding hydroxyl and then hydrolyzed to the corresponding acid of formula I. The reduction proceeds with sodium borohydride, as described above with reference to the reduction of the ketones of formula II. The hydrolysis to the acid may be carried out with an aqueous base such as an alkali metal hydroxide, e.g. sodium hydroxide, in the optional presence of a co-solvent such as methanol or ethanol at temperatures ranging from about room temperature to the reflux or boiling temperature of the solvent used.

Compounds of formula I where $R^3$ and $R^4$ are hydroxy may be prepared from the esters of formula I by elimination of the hydroxyl group to form an olefin. This is accomplished by methods well known in the art by treatment with an acid such as hydrochloric, sulfuric, triflic or preferably toluene sulfonic acid in a solvent such as benzene, acetic acid, dioxane or preferably toluene at about 25° C. to reflux for about 0.5 to 5 hours.

The alkene produced may be hydroxylated using catalytic osmium tetraoxide and an oxidant such as morpholine-N-oxide or the like in a solvent such as ether, THF or preferably acetone mixed with water. The mixture is stirred at room temperature until all the starting material is consumed, which takes anywhere from 1 to 5 hours.

This provides the cis-dihydroxy compounds exclusively. The trans-dihydroxy analogs may be prepared by prolonged oxidation, about 10 to 24 hours, under the same reaction conditions followed by reduction of the 3-hydroxy-4-keto product with a hydride reducing agent such as $LiAlH_4$ or $LiBH_4$ or preferably $NaBH_4$ in a solvent such as THF but preferably MeOH.

The hydroxylated esters are saponified using an alkali metal base with a co-solvent such as lower boiling alcohols, preferably ethanol, to afford the acid products.

The alkene may also be treated with a peroxacid, preferably metachloroperbenzoic acid in a solvent such as THF or, preferably, dichloroethane at about 0° C. to room temperature, preferably 0° C. for 1–5 hours to afford the epoxide. The epoxide is hydrolyzed with $H_2$ and 10% Pd/C in an inert solvent such as ethyl acetate to afford the 3-hydroxy ester ($R^3$=H, $R^4$=OH).

The compounds of formula I wherein $R^1$ is

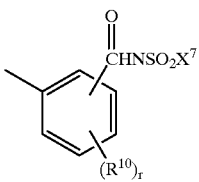

where $R^{10}$ is independently fluoro, chloro, $(C_1-C_6)$alkyl, $(C_1-C_6)$alkoxy, $(C_1-C_4)$perfluoroalkyl, $(C_1-C_4)$perfluoroalkoxy, $(C_1-C_6)$alkylthio, $(C_1-C_6)$alkylsulfinyl, phenylsulfinyl, $(C_1-C_6)$alkylsulfonyl, or phenylsulfonyl and r is 1 or 2, may be obtained by reacting compounds of the formula I wherein $R^1$ is

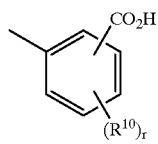

wherein $R^{10}$ and r are as defined above, with a sulfonamide of the formula $X^7SO_2NH_2$ in the presence of a coupling agent such as 1,3-dicyclohexylcarbodiimide or 1-[3-(dimethylamino)propyl]-3-ethyl carbodiimide and in the presence of an organic base such as pyridine, dimethylaminopyridine, triethylamine, diisopropylethylamino or diazobicyclo[5.4.0]undec-7-ene. The reaction is carried out in a solvent such as tetrahydrofuran, diethyl ether, toluene, and chlorobenzene, at a temperature ranging from about room temperature to about the boiling point of the reaction solvent used.

The compounds of formula I where $X^6$ of $R^1$ or aromatic substitution is equal to NHCO—$X^7$, NHSO$_2$—$X^7$ or NHCO—OX$^7$ may be obtained by reaction of compounds of the formula I where $X^5$ or $X^6$ on $R^1$ is carboxy or substituted aromatic or heteroaromatic acid with diphenylphosphoryl azide in a solvent such as toluene, DME, THF or dichloroethane in the presence of benzyl alcohol and an amine base such as pyridine, diisopropylethyl amine, pyrrolidine or, preferably, triethyl amide at the temperature of the boiling point of the solvent used for a time of 5–48 hours, preferably 16 hours. The product from this reaction is hydrogenated in a lower alcohol solvent in the presence of a palladium catalyst, preferably Pd(OH)$_2$/C, followed by acylation with the appropriate acid chloride carbamoyl chloride or sulfonyl chloride.

The synthetic methods outlined above together with the following examples describe methods which were and can be employed to prepare the compounds of this invention.

Where possible, as ascertained by one skilled in the art enabled by this disclosure, pharmaceutically acceptable cationic salts of certain compounds of this invention include but are not limited to, those of sodium, potassium, calcium, magnesium, ammonium, N,N'-dibenzylethylenediamine, N-methylglucamine, ethanolamine and diethanolamine. The pharmaceutically acceptable cationic salts of the compounds of formula I can be prepared by mixing a compound of formula I with one equivalent of an amine base or alkaline metal base.

The compounds of the invention can be administered to mammals, including humans, for the treatment of LTB$_4$ induced illnesses by various routes including oral, parenteral and topical, including the use of suppositories and enemas. On oral administration, dosage levels of about 0.5 to 1000 mg/day, more preferably about 5–500 mg/day may be given in a single dose or up to 3 divided doses. For intravenous administration, dosage levels are about 0.1–500 mg/day, more preferably about 1.0–100 mg/day. Intravenous administration can include a continuous drip. Variations will necessarily occur depending on the age, weight and condition of the subject being treated and the particular route of administration chosen as will be known to those skilled in the art enabled by this disclosure.

The compounds of the invention may be administered alone, but will generally be administered in admixture with a pharmaceutical carrier or diluent selected with regard to the intended route of administration and standard pharmaceutical practice well known to those skilled in the art. For example, they can be administered orally in the form of tablets containing such excipients as starch or lactose, or in capsules either alone or in admixture with excipients, or in the form of elixirs or suspensions containing flavoring or coloring agents. They can be injected parenterally, for example, intramuscularly, intravenously or subcutaneously. For parenteral administration, they are best used in the form of a sterile aqueous solution which can contain other solutes, for example, enough salt or glucose to make the solution isotonic.

The LTB$_4$ activity of the compounds of the invention may be determined by comparing the ability of the compounds of the invention to compete with radio-labelled LTB$_4$ for specific LTB$_4$ receptor sites on guinea pig spleen membranes. Guinea pig spleen membranes are prepared as described by Cheng et al. (J. Pharmacology and Experimental Therapeutics 232:80, 1985). The $^3$H-LTB$_4$ binding assay is performed in 150 $\mu$l containing 50 mM Tris pH 7.3, 10 Mm MgCl$_2$, 9% methanol, 0.7 nM $^3$H-LTB$_4$ (NEN, approximately 200 Ci/mmol) and 0.33 mg/ml guinea pig spleen membranes. Unlabeled LTB$_4$ is added at a concentration 5 $\mu$M to determine non-specific binding. Compounds are added at varying concentrations to evaluate their effects on $^3$H-LTB$_4$ binding. The reactions are incubated at 4° C. for 30 minutes. Membrane bound $^3$H-LTB$_4$ is collected by filtration through glass fiber filters and the amount bound is determined by scintillation counting. The IC$_{50}$ value for a compound is the concentration at which 50% of specific $^3$H-LTB$_4$ binding is inhibited.

The functional activity of the compounds of the invention may be determined in several ways using bioassays. Both high and low affinity forms of the LTB$_4$ receptor have been described that differentially couple to leukocyte chemotaxis and adhesion molecule upregulation respectively (Sterman, J. W.; Groetzl, E. J. et al., J. Immun., 1988, 140, 3900–3904). Human neutrophil chemotaxis is measured as described in Horvath, L. et al., J. Immunol. 1987, 139, 3055. Human neutrophil CD11b upregulation is measured as described in Marder, P. et al., Prostaglandins, Leukotriene Essent. Fatty Acids, 1991, 46, 265–278.

In addition, compounds of formula I can be tested in vivo according to a method analogous to the method described by Pettipler, E. R. et al., Brit. J. Pharmacology, 1993, 423–427, by injecting LTB$_4$ into the dermis of guinea pigs and measuring the blockade of neutrophil migrations into the skin by orally dosed compounds of formula I.

The following Examples illustrate the preparation of the compounds of the invention and are not to be construed as limiting the scope of the invention in any way.

EXAMPLE 1

(5S*,6S*)2-(6-Benzyl-5,6-dihydroxy-5,6,7,8-tetrahydro-naphthalen-2-yl)-4-fluorobenzoic acid A. 2-(4-Fluorophenyl)-4,4-dimethyl-4,5-dihydro-oxazole To a stirred solution of 2-amino-methylpropanol (0.378 mol, 33.64 gm) in 300 ml of methylene chloride at about 0° C. was added a solution of 4-fluorobenzoyl chloride (0.189 mol, 22.35 mL) in 100 mL of methylene chloride over about 0.5 hr. The mixture was allowed to warm to room temperature and stirred for about 3 hrs. The mixture was then poured into water and the layers were separated. The organic phase was washed with two portions of 10% HCl, one portion of saturated sodium chloride solution and dried over anhydrous $MgSO_4$. Removal of the solvent in vacuo afforded a colorless solid which was stirred while $SOCl_2$ (0.567 mol, 41 mL) was added dropwise over about 30 min. The resulting solution was stirred for about 0.5 hr, at which time diethyl ether was added while the solution was stirred rapidly. During this procedure, a colorless precipitate was produced. The slurry was filtered and the solid was washed with three 250 mL portions of diethyl ether. The solid was then dissolved in 300 mL of 3N KOH and the resulting solution was extracted with ethyl acetate. The organic extracts were washed with saturated aqueous NaCl solution and dried over $MgSO_4$. Removal of the solvent in vacuo afforded 32 gm of the title compound of this Example 1A: $^1$HNMR (250 MHz., $CDCl_3$) δ: 8.00–7.91 (m, 2H), 7.10–7.02 (m, 2H), 4.11 (s, 2H), 1.39 (s, 6H).

B. 2-Benzylidene-6-methoxy-3,4-dihydro-2H-naphthalen-1-one

To a stirred solution of 6-methoxy-1-tetralone (0.227 mol, 40 gm) and benzaldehyde (0.272 mol, 27.5 mL) in 450 mL of methanol was added pyrrolidine (0.272 mol, 23.6 mL). The mixture was stirred at room temperature for about 4 days until TLC indicated that no starting tetralone was present. The mixture was concentrated in vacuo, then dissolved in EtOAc, washed with four portions of 10% HCl, two portions of saturated $NaHCO_3$ solution, and one portion of brine. The solvent was removed in vacuo and the crude oil was triturated with diethyl ether to afford 38 g of the title compound of this Example 1B, m.p. 100–102° C. Analysis calculated for $C_{18}H_{16}O_2$: 264.1146. Found: 264.1149.

C. 2-Benzyl-6-methoxy-3,4-dihydro-2H-naphthalen-1-one

A Parr® hydrogenation bottle was charged with chromenone (15 gm), ethyl acetate (150 mL) and 1 g of 10% palladium on charcoal. The mixture was hydrogenated on a Parr® shaker for about 15 hrs under 20 psi of hydrogen. The resulting mixture was filtered through a pad of Celite® and concentrated in vacuo to afford a red oil which was purified by flash chromatography (3:1 hexane/diethyl ether) to afford 14.1 gm of this Example 1C, m.p. 50–51° C. Analysis calculated for $C_{18}H_{18}O_2$: 266.1302. Found: 266.1308.

D. 2-Benzyl-6-hydroxy-3,4-dihydro-2H-naphthalen-1-one

To a stirred solution of the compound of Example 1C (benzyl tetralone) (5 gm, 19 mmol) in methylene chloride (40 mL) at about −78° C. was added boron tribromide (1.95 mL, 21 mmol). The cooling bath was removed and the reaction mixture was stirred overnight at room temperature, after which time an additional 1.5 mL of boron tribromide was added. Stirring was continued at room temperature for about another 4 hrs at which time the mixture was poured into ice water and stirred for about 0.5 hr. The aqueous mixture was saturated with sodium chloride and extracted with four portions of methylene chloride. The layers were separated and the organic phase was washed with water and dried over anhydrous sodium sulfate. Filtration and removal of the solvent in vacuo afforded a brown solid which was purified by flash chromatography (3:2 hexane/ether) to afford 3 gm of the compound of this Example 1D, m.p. 160–162° C. Analysis calculated for $C_{17}H_{16}O_2$: 252.1146. Found: 252.1144.

E. Trifluoromethanesulfonic acid 6-benzyl-5-oxo-5,6,7,8-tetrahdyronaphthalen-2-yl ester To a stirred solution of the compound of Example 1D (2.75 gm, 11 mmol), triethylamine (4.56 mL, 33 mmol) and DMAP (0.05 gm) in methylene chloride (100 mL) at about −78° C. was added trifluoromethanesulfonic anhydride (2 mL, 12 mmol). The cooling bath was removed and the reaction mixture was warmed to room temperature and stirred overnight. The mixture was then poured into ice water and extracted with ethyl acetate. The resulting organic layer was washed with water, dried over anhydrous sodium sulfate, filtered and the solvent was removed in vacuo. The crude product was purified by flash chromatography to afford 3.9 gm of the compound of this Example 1E, m.p. 52–53.7° C. Analysis calculated for $C_{18}H_{15}O_4SF_3$: 384.0638. Found: 384.0602.

F. 2-Benzyl-6-[2-(4,4-dimethyl-4,5-dihydro-oxazol-2-yl)-5-fluorophenyl]-3,4-dihydro-2H-naphthalen-1-one To a stirred solution of n-butyllithium (3.6 mL of a 2.5M solution in hexanes, 9 mmol) in toluene (10 mL) at about −40° C. was added a solution of aryl oxazoline (1.76 gm, 9 mmol) in toluene (5 mL) dropwise via cannula. The mixture was stirred at about −40° C. for about 0.5 hr then warmed to about −25° C. and stirred for about another 1 hr. To this mixture was added zinc chloride (9 mL of a 1M solution in diethyl ether, 0.009 mol). The cooling bath was removed and the mixture was warmed to room temperature and stirred for about 1 hr. The resulting mixture was added via cannula to a solution of the tetralone triflate (3.5 gm, 9 mmol) and palladium tetrakistriphenylphosphine (0.5 mmol, 0.63 gm) in tetrahydrofuran (15 mL). The reaction mixture was heated to reflux for about 2 hr, cooled to room temperature and poured into saturated aqueous ammonium chloride solution. The aqueous mixture was extracted with three portions each of ethyl acetate. The organic phase was washed with three portions of 1M HCl, saturated aqueous sodium bicarbonate and brine. The organic phase was then dried over anhydrous sodium sulfate, filtered an the solvent was removed in vacuo. The crude product was purified by flash chromatography (2:1 diethyl ether/hexane) to afford 2.07 gm of the compound of this Example 1F, m.p. 114–115° C. Analysis calculated for $C_{28}H_{26}NO_2F$: 427.1948. Found: 427.1956.

G. 2-Benzyl-6-[2-(4,4-dimethyl-4,5-dihydro-oxazol-2-yl)-5-fluorophenyl]-1,2,3,4-tetrahydro-naphthalen-1-ol To a stirred solution of the compound of Example 1F (1.5 gm, 3.5 mmol) in methanol (35 mL) was added sodium borohydride (0.20 gm, 5.25 mmol). The resulting brown mixture was stirred at room temperature for about 1 hr, then poured into brine and extracted with three portions of ethyl acetate. The organic phase was dried over anhydrous sodium sulfate and the solvent removed in vacuo to afford 1.20 gm of a 1:1 mixture of cis and trans alcohols, m.p. 88–89° C. Analysis calculated for $C_{28}H_{28}NO_2F$: 429.2087. Found: 429.2067.

H. 2-(6Benzyl-5-hdyroxy-5,6,7,8-tetrahydro-naphthalen-2-yl)-4-fluorobenzoic acid The compound of Example 1G (1.0 gm, 2.34 mmol) was dissolved in 5 mL of methyl iodide and stirred at room temperature for about 2 days, at which time the methyl iodide was removed in vacuo. The residue was taken up in methylene chloride and concentrated in order to remove traces of residual methyl iodide. The dark red residue was dissolved in methanol (5 mL) and 2N NaOH (5 mL) was added. The resulting mixture was heated to reflux with stirring for about 5 hrs. The mixture was then cooled to room temperature and acidified with 3N HCl. The resulting slurry was extracted with three portions of ethyl acetate and the combined organic phase was washed with brine. The organic phase was dried over anhydrous sodium sulfate and the solvent removed in vacuo to afford 0.80 gm of the compound of this Example 1H. $^1$HNMR (250 MHz., methanol-d$_4$) δ: 7.83 (dd, 1H, J=7.0, 7.5), 7.50 (d, 1H, J=7.0), 7.30–7.00 (m, 9H×2), 4.50 (d, 1H, J=2.0), 4.41 (d, 1H, J=8.0), 3.15 (dd, 1H, J=5.4, 13.9), 3.00–2.57 (m, 4H), 2.42 (dd, 1H, J=11.4, 13.5), 2.09–1.35 (m, 5H×2).

I. 2-(6-Benzyl-5-hydroxy-5,6,7,8-tetrahydro-naphthalen-2-yl)-4-fluorobenzoic acid ethyl ester To a stirred solution of the compound of Example 1H (0.80 gm, 2.13 mmol) and ethyl iodide (0.34 mL, 4.26 mmol) in acetonitrile (20 mL) was added potassium carbonate (1.03 gm, 1.45 mmol). The resulting slurry was heated to about 60° C. for about 24 hrs. The mixture was cooled to room temperature, diluted with diisopropyl ether and filtered through celite. Concentration in vacuo afforded 0.72 gm of the compound of this Example 1I as a 1:1 cis/rans mixture. The data for the mixture of diastereomers are as follows: $^1$HNMR (250 MHz., chloroform-d) δ: 7.88 (dd, 1H, J=7.0, 7.5), 7.53 (d, 1H, J=7.0), 7.39–7.70 (m, 9H×2), 4.58–4.52 (m, 1H×2), 4.12 (q, 2H, J=7.0), 4.11 (q, 2H, J=7.0), 3.13 (dd, 1H, J=6.1, 14.2), 3.00 (8H×1, 14H×2), 2.92–2.70 (m, 2H), 2.55 (dd, 1H, J=9.4, 14.2), 2.11–1.40 (m, 5H×2), 1.08 (t, 3H, J=7.0), 1.07 (t, 3H, J=7.0).

J. 2-(6-Benzyl-7,8-dihydro-naphthalen-2-yl)-4-fluorobenzoic acid ethyl ester

To a round bottomed flask containing the compound of Example 1I (0.70 gm) in benzene (50 mL) was added p-toluenesulfonic acid (0.09 gm). The flask was fitted with a Dean-Stark trap to remove water during the course of the reaction. The mixture was heated to reflux for about 16 hrs, then cooled to room temperature and concentrated under reduced pressure. The residue was taken up in chloroform and washed with saturated aqueous sodium bicarbonate. The chloroform extracts were dried over anhydrous sodium sulfate and the solvent was removed in vacuo to afford a yellow oil which was purified by flash chromatography (6:1 hexane/ethyl acetate) to provide 0.56 gm of the compound of this Example 1J. Analysis calculated for $C_{26}H_{23}O_2F$: 386.1676. Found: 386.1713.

K. cis-(5S*,6S*)-2-(6-Benzyl-5,6-dihydroxy-5,6,7,8-tetrahydro-naphthalen-2-yl)-4-fluorobenzoic acid ethyl ester To a stirred solution of the compound of Example 1J (0.50 gm, 1.3 mmol) in 3:1 acetone/water (6 mL) was added N-methylmorpholine-N-oxide (0.168 gm, 1.4 mmol), followed by osmium tetroxide (0.79 mL of a 4% solution in water, 0.1 mmol). The reaction mixture was stirred at room temperature and monitored by TLC for the disappearance of starting material. The mixture was then diluted with chloroform and washed with 10% aqueous NaHSO$_3$ solution. The chloroform extracts were dried over anhydrous sodium sulfate and the solvent was removed under reduced pressure. The residue was purified by flash chromatography (1:1 hexane/ethyl acetate) to give 0.34 gm of this Example 1K, mp 59–60° C. Analysis calculated for $C_{26}H_{25}O_4F$: 420.1736. Found: 420.1722.

L. (5S*,6S*)2-(6-Benzyl-5,-dihydroxy-5,6,7,8-tetrahydro-naphthalen-2-yl)-4-fluorobenzoic acid To a stirred solution of the compound of Example 1K (0.30 gm, 0.71 mmol) in 3:1 methanol/water (12 mL) was added lithium hydroxide monohydrate (0.15 gm, 3.6 mmol). The resulting mixture was heated to reflux for about 4 hrs. The mixture was then cooled to room temperature and acidified with 1N HCl. The aqueous slurry was extracted with ethyl acetate. The organic phase was washed with brine, dried over anhydrous sodium sulfate and the solvent removed in vacuo to afford 0.24 gm of the compound of this Example 1L (the title product), m.p. 127–130° C. Analysis calculated for $C_{24}H_{21}O_4F$: 392.1423. Found: 392.1948.

EXAMPLE 2

7-(2-Carboxy-5-trifluoromethylphenyl)-3-1phenylmethyl-3-hydroxybenzopyran

A. 2',4'-Dihdyroxy-3-chloropropiophenone

To a stirred mixture of resorcinol (200 g, 1.82 mol) and 3-chloropropionic acid (200 g, 1.84 mol) was added trifluoromethane sulfonic acid (1 kg) in one portion. The solution was heated slowly over about 45 minutes to about 80° C. then cooled to room temperature over about 15 minutes and poured into chloroform (4.0 L). The organic portion was slowly poured into water (4.0 L) and the layers separated. The aqueous layer was extracted with chloroform (2×2.0 L). The combined organic layers were washed with brine, dried over sodium sulfate and filtered. Concentration in vacuo gave as an orange semi-solid (244.1 g) which was used crude in the next step. $^1$H-NMR (300 MHz, CDCl$_3$): 12.56 (1H, s), 7.63 (1H, d, J=7.6), 6.37–6.46 (2H, m), 3.92 (2H, t, J=6.3), 3.41 (2H, t, J=6.3).

B. 7-Hydroxybenzopyran-4-one

To a cooled (about 5° C.) solution of 2N sodium hydroxide (10.0 L) was added the compound of Example 2A (244.1 g) in one portion. The solution was warmed to room temperature over about 2 hours using a warm water bath then recooled to about 5° C. and the pH adjusted to 2 with 6 M sulfuric acid (1.2 L). The mixture was extracted with 3×3.0 L of ethyl acetate, washed with brine (1×2.0 L) dried over sodium sulfate and filtered. Concentration in vacuo gave a tan solid. Trituration with hexanes, and filtration afforded 173.7 g (58% yield) of this Example 2B. M.P. 136–137° C.

C. 7-[Trifluoromethylsulfonyloxy]-benzopyran-4-one

To a stirred solution of the compound of Example 2B (173.7 g, 1.05 mole) in methylene chloride (3.0 L) at about −78° C. was added triethylamine (320 g, 3.16 mole) and dimethylaminopyridine (2.5 g). After total dissolution, trifluoromethane sulfonic anhydride (327 g, 1.16 mole) was added dropwise over about 20 minutes, the material was stirred for about 30 minutes at about −78° C., and then warmed to room temperature over about 2 hours. The reaction mixture was poured into saturated ammonium chloride solution (2.5 L) and the layers separated. The aqueous layer was extracted with 2×2.0 L of methylene chloride. The combined organic fractions were washed with water (1×1.0 L), dried over magnesium sulfate and filtered. Concentration in vacuo gave a red oil. Chromatography over silica gel (1 kg) eluting with (8:1) hexane: ethyl acetate gave after solvent removal 211.1 g. (69% yield) of the title product of this Example 2C. M.P. 43–44 ° C.

D. 7-[(Trifluoromethylsulfonyl)oxy]-3-phenylmethylene-benzopyran-4-one

To a stirred solution of the product of Example 2C (27 g, 91.2 mmole) in 183 mL of methanol was added benzaldehyde (11.1 mL, 109 mmole) followed by pyrrolidine (9.1 mL, 109 mmole). The mixture was stirred at room temperature overnight, cooled to about 0° C. and filtered. The solid was washed once with 50 mL of ice-cold methanol and then dried in vacuo; 35.2 g, (75% yield) of the title product of this Example 2D was recovered. M.P. 133–135° C. $^1$H NMR (300 MHz, CDCl$_3$): 8.11 (1H, d, J=8.7), 7.91 (1H, bs), 7.40–7.51 (2H, m), 7.24–7.38 (3H, m), 6.97 (1H, dd, J=8.7, 2.4), 6.91 (1H, d, J=2.4), 5.40 (1H, bs).

E. 7-[(Trifluoromethylsulfonyl)oxy]-3-phenylmethyl-benzopyran-4-one

To a solution of the compound of Example 2D (26.6 g, 69.2 mmole) in 250 mL of ethyl acetate in a 500 mL Parr® shaker flask was added 10% palladium on carbon catalyst (1.3 g). The mixture was hydrogenated at 40 psi until hydrogen uptake ceased after about 3 hours. The mixture was filtered through Celite® (a tradename for diatomaceous earth) to remove the palladium catalyst, and chromatographed over silica gel (hexane-ether); 25.1 g (94% yield) of the title product of this Example 2E was obtained. M.P. 56–58° C. $^1$H NMR (300 MHz, CDCl$_3$): 8.01 (1H, d, J=8.5), 7.20–7.35 (5H, m), 6.81–6.96 (2H, m), 4.42 (1H, dd, J=11.6, 4.4), 4.22 (1H, dd, J=11.6, 8.7), 3.26 (1H, dd, J=14.0, 4.4), 2.90–3.05 (1H, m), 2.70 (1H, dd, J=14.0, 8.7).

F. 7-(2-Carboethoxy-5-trifluoromethylphenyl)-3-phenylmethyl-3,4-dihydrobenzopyran Using the procedure described in Examples 1F–1J, but using 2-(4-trifluoromethylphenyl)-4,4-dimethyl4,5-dihydro-oxazole as a reactant, yielded the desired product of this Example 2F. $^1$HNMR (300 MHz, CDCl$_3$) δ: 7.87 (1H, d, J=8.0), 7.68–7.61 (2H, m), 7.41–7.22 (5H, m), 6.97 (1H, d, J=7.8), 6.85–6.73 (2H, m), 6.21 (1H, s), 4.20 (2H, q, J=7.2), 3.48 (2H, s), 1.15 (4H, t, J=7.2).

G. 7-(2-Carboethoxy-5-trifluoromethylphenyl)-3-phenylmethyl-3,4-oxiranobenzopyran To a solution of the olefin from Example 2F (230 mg, 0.53 mmol) in methylene chloride at about 0° C. was added m-CPBA (89 mg, 0.53 mmol). After about 1 hr, the mixture was diluted with ether and washed with 1N NaOH solution and brine. The organic layer was the dried (MgSO$_4$), filtered and concentrated. Purification by flash chromatography (elution with 3:1 hexane-ethyl acetate) afforded the corresponding epoxide of this Example 2G (209 mg, 87%). The product was used immediately for the next step.

H. 7-(-2-Carboethoxy-5-trifluoromethylphenyl)-3-phenylmethyl-3-hydroxy)benzopyran To a solution of the epoxide of Example 2G (150 mg, 0.33 mmol) in ethyl acetate was added 10% Pd on carbon (100 mg). The system was fitted with a balloon containing H$_2$ and the flask was purged several times. After stirring for about 16 hrs, the solution was filtered and concentrated. Flash chromatography elution with 5:1 hexane-ethyl acetate provided the desired alcohol of this Example 2H (80 mg, 53%). $^1$HNMR (300 MHz, CDCl$_3$) δ: 7.89 (1H, d, J=8.0), 7.70–7.62 (2H, m), 7.42–7.25 (5H, m), 7.07 (1H, d, J=7.8), 6.90–6.80 (2H, m), 3.95 (2H, s), 4.19 (2H, q, J=7.1), 3.04–2.72 (4H, m).

I. 7-(2-Carboxy-5-trifluoromethylphenyl)-3-phenylmethyl-3-hydroxybenzopyran

Saponification of the compound of Example 2H analogous to the procedure described in Example 1L afforded the desired product of Example 2. $^1$HNMR (300 MHz, CDCl$_3$) δ: 7.98 (1H, d, J=7.8), 7.67–7.64 (2H, m), 7.38–7.26 (5H, m), 7.06 (1H, d, J=7.8), 6.88–6.85 (2H, m), 2.99–2.72 (4H, m).

EXAMPLE 3

(3S*,4R*)-7-(2-Carboxy-5-trifluoromethyl-3,4-dihydroxy)-3-phenylmethyl-benzopyran A. 7-(Carboethoxy-5-trifluoromethylphenyl)-3-phenylmethyl-3-hydroxybenzopyran-4-one To a solution of the olefin from Example 2F (3.7 g, 8.44 mmol) in acetone-water (3:1) was added N-methylmorpholine-N-oxide (3.0 g, 25.3 mmol) followed by OSO$_4$. After stirring overnight, the solution was diluted with water and extracted with ethyl acetate. The combined extracts were dried and concentrated. Purification of the residue by flash chromatography afforded the corresponding hydroxy ketone of this Example 3A (3.0 g, 76%). M.P.: 85–87° C.

B. (3S*,4R*)-7-(2-Carboethoxy-5-trifluoromethlphenyl)-3,4-dihydroxy-3-phenylmethyl-benzopyran To a solution of the ketone of Example 3A (3.0 g, 6.4 mmol) in methanol (50 mL) at room temperature was added NaBH$_4$ (250 mg, 6.4 mmol). After about 30 min. the reaction was quenched (NH$_4$Cl sol.), extracted (ethyl acetate), dried (MgSO$_4$), filtered and concentrated. Flash chromatography (elution with 2:1 hexane-ethyl acetate) provided the desired trans-diol of this Example 3B (2.9 g, 97%). $^1$HNMR (300 MHz, CDCl$_3$) δ: 7.89 (1H, d, J=8.0), 7.69–7.55 (2H, m), 7.42–7.20 (5H, m), 6.90–6.82 (2H, m), 4.43 (1H, s), 4.15 (1H, d, J=12.1), 3.90 (1H, d, J=12.1), 3.79 (3H, s), 3.13 (1H, d, J=13.5), 2.85 (1H, d, J=13.5).

C. (3S*,4R*)-7-(2-Carboxy-5-trifluoromethyl-3,4-dihydroxy)-3-phenylmethylbenzopyran Saponification of the compound from Example 3B analogously to the procedure described in Example 1L afforded the desired acid of this Example 3. M.P.: 100–102° C.

EXAMPLE 4

(3S*,4S*)-7-(2-Trifluoromethanesulfonylamino-5-fluoro)-3,4-dihydroxy-3-hydroxy-3-phenylmethyl-2H-1-benzopyran A. 7-[(5-fluoro-(2-(4,4-dimethyl-2-oxazolinyl)phenyl]-3-phenylmethylene-1-benzopyran-4-one To a stirred solution of 2-(4-fluorophenyl)-4,4-dimethyl-2-oxazoline (1.0 eq in tetrahydrofuran, 0.5M concentration) at about –78° C. under N$_2$ was added n-butyllithium in hexanes (1.1 eq., 2.5M solution). The mixture was stirred at about –78° C. for about 1 hour, then ZnCl$_2$ (1M solution in ether, 1.1 eq.) was added. The mixture was warmed to about 10° C. over about 1 hour to give 2-(4-fluorophenyl-2-chlorozinc)-4,4-diethyl-2-oxazoline (not isolated). To this solution was added 7-[((trifluoromethyl)sulfonyl)oxy]-3-phenylmethylene-1-benzopyran-4-one (1.0 eq.) and Pd(PPh$_3$)$_4$ (0.02 eq.). The mixture was refluxed (about 68° C.) for about 3 hours, cooled to room temperature and poured into NH$_4$Cl solution. The solution was extracted with 3 times with diethyl ether and the combined organic fraction dried over MgSO$_4$. Filtration followed by solvent removal in vacuo and column chromatography (silica gel—2:1 hexane:ether) gave the title compound of this Example 4A as a yellow solid, 65% yield, m.p. 110–112° C. $^1$H-NMR (300 MHz, CDCl$_3$): 8.04 (1H, d), 7.91 (1H, s), 7.78 (1H, dd), 7.41–7.52 (3H,m), 7.31 (2H, d), 7.06–7.18 (3H, m), 7.02 (1H, s), 5.40 (2H, s), 3.86 (2H, s), 1.31 (6H, s).

B. (3S*,4R*)7-[5-fluoro-(2-(4,4-dimethyl-2-oxazolinyl)phenyl]-4-hydroxy-3-phenylmethyl-2H-1-benzopyran To a stirred solution of the compound from Example 4A in THF (0.1M) at about 0° C. was added LiAlH$_4$ (1M in ether, 2.2 eq) dropwise over about 10 minutes. The mixture was warmed to room temperature and stirred for about 12 hours. The mixture was cooled to about 0° C., quenched with Rochelles salt, and filtered through diatomaceous earth. The aqueous layer was extracted twice with ethyl acetate, and the combined organic layers were washed with brine and dried over MgSO$_4$. Filtration and solvent removal afforded a yellow oil. Chromatography over silica gel (ethyl acetate:hexane) afforded a 60% yield of the title compound of this Example 4B as a white solid. M.P. 65–70° C. (decomposed). Anal. calcd. for C$_{27}$H$_{26}$NO$_3$F: C, 75.15; H, 6.07; N, 3.25. Found: C, 74.75; H, 6.02; N, 3.09. $^1$H-NMR (300 MHz, CDCl$_3$) δ: 7.70 (1H, dd), 7.02–7.37 (8H, m), 6.96 (1H, dd), 7.91 (1H, d), 4.51 (1H, d), 4.23 (1H, dd), 4.39 (1H, dd) 3.87 (2H, dd), 2.74 (1H, dd), 2.55 (1H, dd), 2.18–2.28 (1H, m) 1.31 (6H, d).

C. (3S*,4R*)7-(2-Carboxy-5-fluorophenyl)-4-hydroxy-3-phenylmethyl-2H-1-benzopyran The compound from Example 4B was dissolved in methyl iodide (0.5M) at room temperature and stirred for about 24 hours. The methyl iodide was removed in vacuo, the oily solid was dissolved in CH$_2$Cl$_2$ and the solvent removed in vacuo. This operation was repeated to remove traces of methyl iodide. The solid was dissolved in methanol (0.5M) and 2M NaOH (0.5M) was added. The mixture was refluxed for about 5 hours, cooled to room temperature and acidified to pH 2 with 1M HCl. The mixture was extracted twice with ethyl acetate, washed with brine, and dried over MgSO$_4$. Filtration and solvent removal in vacuo, followed by chromatography (silica gel, 10:1 methylene chloride:methanol) gave the desired acid of this Example 4C, 93% yield. $^1$H-NMR (300 MHz, CD$_3$COCD$_3$) δ: 7.80 (1H, dd), 7.48 (1H, d), 7.18 (7H, m), 7.13 (1H, dd), 6.91 (1H, dd), 6.80 (1H, d), 4.52 (1H, d), 4.23 (1H, dd), 3.96 (1H, dd), 2.89 (1H, dd), 2.54 (1H, dd), 2.19–2.30 (1H, m).

D. (3S*,4S*)-7-(2-Carboxy-5fluorophenyl)-3,4-dihydroxy-3-phenylmethyl-2H-1-benzopyran Using procedures of Examples 1I to 1L, the title compound of this Example 4D was prepared from the compound of Example 4C.

E. (3S*,4S*)-7-(2-Carbobenzyloxyamino-5-fluoro)-3,4-dihydroxy-3-phenylmethyl-2H-1-benzopyran To a solution of the compound prepared in Example 4D (1 mmole) in 10 mL of 1,4-dioxane was added 1.05 equivalents of diphenylphosphorylazide, 1.1 eq. of benzyl alcohol and 2.2 equivalents of triethylamine. The mixture was refluxed for about 16 hours, the solvent removed under vacuum and the residue chromatographed over silica gel (1:1-hexane:EtOAc) to afford the N-CBZ product of this Example 4E. $^1$H-NMR (300 MHz, CDCl$_3$) δ: 8.02 (1H, s), 7.39–7.22 (1H, m), 7.03 (1H, dt, J=7, 2), 6.95–6.87 (2H, m), 6.83 (1H, s), 5.11 (2H, s), 4.48 (1H, s), 3.98 (1H, d, J=10.1), 3.80 (1H, d, J=10.1), 2.89 (2H, s).

F. (3S*,4S*)-7-(2-Trifluoromethanesulfonylamino-5-fluoro)-3,4-dihydroxy-3-hydroxy-3-phenylmethyl-2H-1-benzopyran To a solution of the compound prepared in Example 4E in 10 mL of EtOH was added 0.05 eq. by weight of Pd(OH)$_2$ and the slurry was hydrogenated on a Parr® shaker apparatus at 1 Atm. for about 3 hours. The mixture was filtered through Celite® and the filtrate evaporated. The yellow oil was redissolved in CH$_2$Cl$_2$ (10 mL), cooled to about 0° C. and triethylamine (2.2 eq) added, followed by trifluoromethanesulfonic anhydride (1.1 eq). After stirring for about 2 hours, 2 equivalents of solid NaOMe was added, the reaction stirred for about 15 minutes, and H$_2$O added (10 mL). The mixture was adjusted to pH 2 with 0.1M HCl then extracted with 3×10 mL EtOAc. The combined organic layers were washed with brine, dried over MgSO$_4$, filtered and solvent removed under vacuum to afford a yellow semisolid. Chromatography over silica gel (1:1–10:1 EtOAc-Hexane) gave the desired sulfonamide of this Example 4F. M.P.: 55–57° C.

EXAMPLE 5

1-(3S,4S)-((3-(4-phenyl-phenylmethyl)-3-hydroxy)-4-hydroxy)-chroman-7-yl)cyclopentane carboxylic acid A. Ethyl 1-(3-(4-phenyl-phenylmethyl)-4-chromanon-7-yl)cyclopentanecarboxylate 3-(4-Phenyl-benzyl)-7-trifluoromethylsulfonyloxy-4-chromanone (35.0 g, 91.0 mmole, prepared from the product of Example 2C with biphenyl aldehyde using the procedures of Example 2D and Example 2E, was dissolved in a mixture of dimethylformamide (230 mL) and dimethoxyethane (230 mL). To this solution was added in the following order, tris(2-methylphenyl)phosphine (7.48 g, 24.6 mmole), bis (benzonitrile)palladium (II) chloride (2.44 g, 6.37 mmole), the trimethylsilyl ketene acetal of ethyl cyclopentanecarboxylate (29.26 g, 136.5 mmole), and a 1.0M ethereal solution of zinc chloride (25 mL, 25 mmole). The resulting clear yellow solution was refluxed for about 1 hour. Additional trimethylsilyl ketene acetal (9.75 g, 45.5 mmole) was added at this point and the reflux continued for about another 1 hour. The cooled mixture was diluted with water (1 L) and extracted with ether. The combined ether extracts were washed with water (1 L) and then dried over magnesium sulfate. Filtration and concentration of the extract gave a yellow oil which was chromatographed on silica gel (8:92 ethyl acetate/hexane). This yielded 22.13 g (64%) of the title compound of this Example 5A as a white solid; m.p. 50–56° C.; $^1$H NMR (CDCl$_3$): 1.23 (3H, t, J=7.0), 1.75 (4H, m), 1.9 (2H, m), 2.6 (2H, m), 2.70 (1H, dd, J=10.5, 13.8), 2.9 (1H, m), 3.26 (1H, dd, J=4.3, 13.8), 4.08 (2H, d, J=7.0), 4.15 (1H, dd, J=8.2, 11.5), 4.35 (dd, J=4.3, 11.5), 6.95 (1H, d, J=1.7), 7.02 (1H, dd, J=1.7, 8.3), 7.2–7.4 (5H, m) 7.84 (1H, d, J=8.3).

B. Ethyl 2-(4-hydroxy-3-(4-phenyl-phenylmethyl) chroman-7-yl).cyclopentane carboxylate The compound of Example 5A (111.99 g, 295.9 mmole) was dissolved in ethanol (2.5 L) and cautiously treated with sodium borohydride (12.3 g, 325.5 mmole) at room temperature. After about 3 hours the reaction mixture was concentrated to a small volume and diluted with ether. The ether was washed with saturated sodium bicarbonate solution and dried over sodium sulfate. The extract was filtered and concentrated to an oil which was chromatographed on silica gel (20:80—ethyl acetate/hexane). This gave 63.4 g (56%) of the higher R$_1$ product, i.e. 3R*,4R*, as an oil: $^1$H NMR (CDCl$_3$) δ: 1.15 (t, J=7.1, 3H), 1.7 (m, 4H), 1.8–1.9 (m, 2H), 2.3 (m, 1H), 2.5–2.6 (m, 2H), 2.66 (dd, J=7.2, 13.6, 1H), 2.86 (dd, J=8.4, 13.6, 1H), 4.0–4.1 (m, 4H), 4.47 (br t, 1H), 6.85 (d, J=1.8, 1H), 6.88 (dd, J=1.8, 7.9, 1H), 7.12 (d, J=7.9, 1H), 7.1–7.35 (m, 5H); and 43.3 g (38%) of the lower R$_1$ product, i.e. 3S*,4R* as an oil: $^1$H-NMR (CDCl$_3$) δ: 1.17 (t, J=7.0, 3H), 1.7 (m, 4H), 1.8–1.9 (m, 2H), 2.2 (m, 1H), 2.52 (dd, J=9.3, 13.7, 1H), 2.6 (m, 2H), 2.70 (dd, J=6.3, 13.7, 1H), 3.95 (dd, J=3.7, 11.2, 1H), 4.07 (q, J=7.0, 2H), 4.18 (dd, J=2.6, 11.2, 1H), 4.47 (br t, 1H), 6.88 (d, J=1.8, 1H), 6.94 (dd, J=1.8, 8.0, 1H), 7.15–7.3 (m, 6H).

C. 1-(3S,4S)-((3-(4Phenyl-phenylmethyl)-3-hydroxy)-4-hydroxy)-chroman-7-yl)cyclopentane carboxylic acid The desired product was obtained from the cis and trans mixture of the compound of Example 5B by reacting the compound of Example 5B analogously to the procedures described in Examples 1J–1L to produce the title compound of this Example 5. M.P.: 185–187° C.

EXAMPLE 6

(3S,4S)-7-(Carboxy-5-trifluoromethylphenyl)-3,4-dihydroxy-3-phenylmethyl-benzopyran A. 7-(2-Carbomethoxy-5-trifluoromethylphenyl)-4-L-t-Boc-tryptophane ester-3-hydroxy-3-phenylmethyl) benzopyran To a solution of (3S,4S)-7-(2-carbomethoxy-5-trifluoromethylphenyl)-3,4-dihydroxyl-3-phenylmethylbenzopyran (225 mg; 0.49 mmol) in CH$_2$Cl$_2$ (6 mL) was added t-BOC-L-tryptophan (223 mg; 0.74 mmol), DMAP (120 mg; 0.98 mmol), and EDCI (165 mg; 0.86 mmol). After stirring for about 16 hrs, the solution was diluted with ethyl acetate and washed with 1N HCl and brine, dried (MgSO$_4$), filtered and concentrated. Purification of the residue by flash chromatography (elution with hexane-ether-methylene chloride 3:1:6) afforded 137 mg, 38% of the faster running diastereomer followed by 135 mg, 37% of the slower running diastereomer of this Example 6A. $^1$H-NMR (300 MHz, CDCl$_3$) δ: LP isomer: 8.98 (1H, s), 8.00 (1H, d, J=8.0), 7.76–7.67 (2H, m), 7.68 (1H, d, J=7.5), 7.40 (1H, d, J=7.6), 7.37–7.09 (9H, m), 6.92–6.86 (2H, m), 6.61 (1H, s), 5.80 (1H, s), 4.93 (1H, d, J=6.3), 4.57 (1H, dd, J=6.5, 3.0), 3.91 (2H, s), 3.82 (1H, d, 10.2), 3.72 (1H, d, J=10.2), 3.50 (1H, dd, J=15.7, 5.0), 3.25 (1H, dd, J=15.0, 6.1), 2.84 (2H, s), 1.39 (9H, s). MP isomer: 8.72 (1H, s), 8.03 (1H, d, J=7.9). 7.78–7.71 (2H, m), 7.59 (1H, d, J=8.0), 7.32–7.05 (9H, m), 6.93–6.80 (2H, m), 6.41 (1H, m), 5.60 (1H, s), 5.17 (1H, d, J=6.0), 4.68–4.58 (1H, m), 3.95 (2H, s), 3.65 (1H, d, J=10.3), 3.43 (1H, d, 10.2), 3.30 (1H, dd, J=15.1, 5.3), 3.13 (1H, dd, J=15.0, 7.9), 2.72 (2H, s), 1.49 (9H, s).

B. (3S,4S)-7-(2-Carbomethoxy-5-trifluoromethylphenyl)-3,4-dihydroxyl-3-phenylmethyl-benzopyran To a solution of the higher R$_1$ t-Boc tryptophan ester of Example 6A (130 mg; 0.17 mmol) in methanol-THF (7 mL ca. 5:2) was added 1N NaOH (175 mL, 1N). After about 1 hr the solution was diluted with ethyl acetate, washed with 1N HCl and brine, dried (MgSO$_4$), filtered and concentrated. Purification by flash chromatography (elution with hexane-ether-methylene chloride 2:1:6) afforded the corresponding alcohol of this Example 6B (63 mg, 80%). $^1$HNMR (300 MHz, CDCl$_3$) δ: 7.94 (1H, d, J=7.8), 7.72–7.60 (2H, m), 7.46 (1H, d, J=8.0), 7.40–7.22 (4H, m), 6.97–6.85 (3H, m), 4.02 (1H, d, J=12.1), 3.86 (1H, d, J=10.1), 3.72 (3H, s), 2.93 (2H, s), 2.48 (1H, bs).

C. (3S,4S)-7-(Carboxy-5-trifluoromethylphenyl)-3,4-dihydroxy-3phenylmethylbenzopyran To a solution of the ester of Example 6B (60 mg; 0.13 mmol) in methanol (3 mL) was added NaOH (3 mL; 3N). After heating at about 60° C. for about 1 hr, the mixture was cooled and acidified with 1N HCl. The solution was extracted with ether and the combined extracts were washed with brine, dried (MgSO$_4$), filtered and concentrated to give the essentially pure acid of this Example 6 (46 mg, 80%), which was purified further by recrystallization from hexane-ethyl acetate. M.P.: 90–92° C.

EXAMPLE 7

7-(2-Carboethoxy-5-fluoro-phenyl)-4-hydroxy-3-(4-phenyl-phenylmethyl)-benzopyran A. 7-(Trimethylstannyl)-3-(4-phenyl-phenylmethyl)-benzopyran4-one To a stirred solution of the compound prepared in Example 2E (10.95 g, 25.0 mmole) in 200 mL of dioxane was added lithium chloride (3.20 g, 75.0 mmole), Pd(PPh$_3$)$_4$ (1.15 g, 1.0 mmole), 3 crystals of butylated hydroxytoluene, and hexamethylditin (9.0 g, 27.5 mmole). The mixture was heated to reflux for about 1.5 hours, cooled to room temperature and poured into 150 mL of saturated, aqueous ammonium chloride solution. The mixture was extracted with 3×150 mL of diethylether and the combined organic fractions were washed with brine, dried over sodium sulfate and filtered. Evaporation in vacuo gave a yellow semi solid which was chromatographed over silica gel (5:1 hexane:ether) to give 9.8 g (89% yield) of the title product of this Example 7A. $^1$H NMR (300 MHz, CDCl$_3$) δ: 7.85 (1H, d, J=8.7), 7.18– 7.37 (9H, m), 7.14 (1H, d, J=8.7), 7.11 (1H, s), 4.38 (1H, dd, J=11.6, 4.5), 4.17 (1H, dd, J=11.6, 8.4), 3.28 (1H, dd, J=14.0, 4.4), 2.84–2.95 (1H, m), 2.71 (1H, dd, J=14, 11), 0.31 (9H, s).

B. 7-(2-Carboethoxy-5-fluoro-phenyl)-3-(4-phenyl-phenylmethyl)-benzopyran-4-one

To a stirred solution of the compound of Example 7A (8.28 g, 17.5 mmole) in dimethylformamide (DMF) (35 mL) was added Pd(PPh$_3$)$_2$Cl$_2$ (490 mg, 0.7 mmole), 3 crystals of BHT and ethyl-2-iodo-5-fluorobenzoate (5.4 g, 19.1 mmole). The mixture was stirred at reflux for about 1.5 hours, cooled to room temperature and poured into 150 mL of saturated aqueous ammonium chloride solution. The mixture was extracted with 3×150 mL of diethyl ether, and the combined extract was washed with 2×100 mL of water, and then brine. The solution was dried over sodium sulfate, filtered and evaporated in vacuo to afford a yellow oil. Chromatography over silica gel (4:1 hexane:ether elution) afforded 6.51 g of the title compound of this Example 7B as a viscous oil. $^1$H NMR (300 MHz, CDCl$_3$) δ: 7.95 (2H, m), 7.28–7.65 (9H, m), 6.92–7.22 (4H, m), 4.49 (1H, dd, J=11.6, 4.5), 4.29(1H, dd, J=11.6, 8.5), 4.15 (2H, q), 3.31 (1H, dd, J=14.0, 4.4), 2.91–2.99 (1H, m), 2.73 (1H, dd, J=14.0, 11.1), 1.20 (3H, t).

C. 7-(2-Carboethoxy-5-fluoro-phenyl)-4-hydroxy-3-(4-phenyl-phenylmethyl)benzopyran To a stirred solution of the compound of Example 7B (6.60 g, 17.5 mmole) in 35 mL of methanol at room temperature was added sodium borohydride (940 mg, 26.0 mmole) in one portion. The dark mixture was stirred at room temperature for about 2 hours then poured into saturated aqueous ammonium chloride solution (75 mL) and extracted with 3×75 mL of diethyl ether. The combined extracts were washed with brine, dried over sodium sulfate, filtered and concentrated in vacuo to give an off-yellow oil. Chromatography on silica gel eluting with 4:1 hexane:ether afforded first 3.26 g of the cis ring isomer of the title compound of this Example 7, and then 1.98 g of the trans isomer of the title compound of this Example 7 as viscous oils, total yield 81%. Cis ring isomer: $^1$H NMR (300 MHz, CDCl$_3$) δ: 7.95 (1H, dt), 6.8–7.61 (14H, m), 4.58 (1H, t, J=7.2), 4.28 (1H, dd, J=9.1, 2.5), 4.03 (1H, dd, J=9.1, 5.4), 4.15 (2H, q), 2.78 (1H), 2.77 (1H, dd, J=13.7, 6.2), 2.58 (1H, dd, J=13.7, 9.1), 2.20–2.29 (1H, m), 1.83 (1H, d, J=7.2), 1.1 (3H, t). Trans ring isomer: $^1$H NMR (300 MHz, CDCl$_3$) δ: 7.95 (1H, dt), 6.8–7.60 (14H, m), 4.56 (1H, dt, J=4.7, 3.8), 4.12–4.19 (2H, m), 4.10 (2H, q), 2.90 (1H, dd, J=13.6, 8.4), 2.70 (1H, dd, J=13.6, 7.2), 2.36–2.39 (1H, m), 1.75 (1H, d, J=4.7), 1.12 (3H, t).

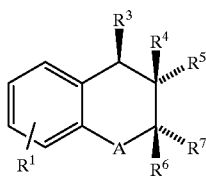

The compounds of Examples 8–16 were synthesized analogously to the synthetic method indicated, using the appropriate corresponding starting materials.

| Ex. No. | Prep. Method | A | R¹ | R³ | R⁴ | R⁵ | R⁶ | R⁷ | Data |
|---|---|---|---|---|---|---|---|---|---|
| 8 | 1L | O | 7-(2-CO₂H, 4-CF₃)phenyl | OH | OH | Bn | H | H | M.P.: 95–96° C. |
| 9 | 1L | O | 7-(2-CO₂H, 4-CF₃)phenyl | OH | OH | 4-phenyl-Bn | H | H | M.P.: 189–191° C. |
| 10 | 1L | O | 7-(2-CO₂H, 4-F)phenyl | OH | OH | Bn | H | H | M.P.: 90–92° C. |
| 11 | 1L | O | 7-(2-CO₂H, 4-F)phenyl | OH | OH | 4-phenyl-Bn | H | H | M.P.: 160° C. |
| 12 | Ex. 1 | O | 7-(2-CO₂H, 4-Cl)phenyl | OH | OH | Bn | H | H | ¹HNMR (250 MHz., chloroform-d)δ: 7.91 (d, 1H, J = 8.0), 7.47–7.22 (m, 8H), 6.91 (dd, 1H, J = 1.0, 7.0), 6.81 (s, 1H), 4.50 (s, 1H), 3.98 (d, 1H, J = 11.5), 3.81 (d, 1H, J = 11.5), 2.91 (s, 2H). m.p. = 102.9–104.5° C. |
| 13 | Ex. 1 | O | 7-(2-CO₂H, 4-Cl)phenyl | OH | OH | 4-phenyl-OH | H | H | ¹HNMR (8.00 MHz., DMSO-d₆)δ: 7.76–7.27 (m, 13H), 6.92 (d, 1H, J = 9.3), 6.78 (s, 1H), 5.68 (br s, 1H), 4.71 (br s, 1H), 4.35 (s, 1H), 3.90 (d, 1H, J = 13.1), 3.73 (d, 1H, J = 13.1), 2.79 (AB quartet, 2H, J = 14.6). m.p. = 178.5–179.9° C. |

-continued

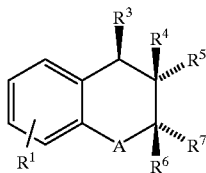

The compounds of Examples 8–16 were synthesized analogously to the synthetic method indicated, using the appropriate corresponding starting materials.

| Ex. No. | Prep. Method | A | R¹ | R³ | R⁴ | R⁵ | R⁶ | R⁷ | Data |
|---|---|---|---|---|---|---|---|---|---|
| 14 | 4E | O | 7-, HNSO₂CF₃, F (phenyl) | OH | OH | 4-phenyl-Bn | H | H | M.P.: 70–72° C. |
| 15 | 1L | O | 7-, CO₂H, CF₃ (phenyl) | OH | OH | Bn | Me | Me | M.P.: 153–154° C. |
| 16 | * | O | 7-, CO₂H, CF₃ (phenyl) | OH | OH | —CH(OH)Bn | H | H | Dec. Pt. 220° C. |

*This compound was synthesized analogously to steps of Example 7B then Example 7C and finally Example 1K.

What is claimed is:
1. A compound of the formula

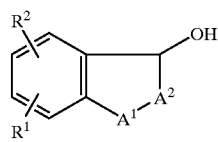

(I)

or the pharmaceutically acceptable salts thereof wherein
$A^1$ is $CH_2$, and NH or $N(C_1-C_6)$alkyl;

$A^2$ is

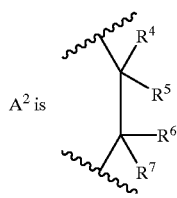

$R^4$ is hydrogen or hydroxy;
$R^5$ is selected from the group consisting of $—(CH_2)_nX^{10}$ and $—CH(OH)X^{10}$;
wherein
n is 0, 1, 2, or 3;
$X^{10}$ is $(C_3-C_8)$cycloalkyl or one of the following optionally substituted rings: phenyl, thienyl, pyridyl, furyl, naphthyl, quinolyl, isoquinolyl, pyrimidinyl or pyrazinyl;
where the optionally substituted rings are optionally substituted with one or two substituents independently selected from the group consisting of fluoro, chloro, $(C_1-C_6)$alkyl, $(C_1-C_6)$alkoxy, $(C_1-C_4)$perfluoroalkyl, $(C_1-C_4)$perfluoroalkoxy, and optionally substituted phenyl;
where the optionally substituted phenyl is optionally substituted with one or two substituents independently selected from the group consisting of fluoro, chloro, $(C_1-C_6)$alkyl, $(C_1-C_6)$alkoxy, $(C_1-C_4)$perfluoroalkyl, $(C_1-C_4)$perfluoroalkoxy,
$R^6$ and $R^7$ are each independently hydrogen or $(C_1-C_4)$alkyl or $R^6$ and $R^7$ are taken together with the carbon atom to which they are attached and form a $(C_4-C_7)$cycloalkyl;
$R^1$ is selected from the group consisting of tetrazolyl, carboxy,
$—(CH_2)_mCX^3X^4X^5$, and a substituted five or six membered aromatic ring optionally having one or two heteroatoms where the heteroatomrs are optionally independently selected from the group consisting of O, S and N;
wherein
m is 0, 1 or 2;
$X^3$ and $X^4$ are each independently hydrogen or $(C_1-C_6)$alkyl or $X^3$ and $X^4$ are taken together with the carbon atom to which they are attached and form a $(C_3-C_7)$cycloalkyl;
$X^5$ is hydroxy, carboxy, or tetrazolyl;
the substituted five or six membered aromatic ring is substituted with one substituent selected from the group consisting of carboxy, tetrazolyl, $—CO—N$(H)($SO_2—X^7$), $—N(H)(SO_2—X^7)$, $—N(H)(CO—X^7)$, and $—N(H)(CO—O$ lower alkyl) and with one or two substituents each independently selected from the group consisting of fluoro, chloro, $(C_1-C_6)$alkyl, $(C_1-C_6)$alkoxy, $(C_1-C_4)$perfluoroalkyl, $(C_1-C_4)$perfluoroalkoxy; wherein
$X^7$ is $—CF_3$, $(C_1-C_6)$alkyl, $(C_3-C_6)$cyclo-alkyl or one of the following optionally substituted rings: phenyl, thienyl, pyridyl, furyl, naphthyl, quinolyl, isoquinolyl, pyrimidinyl or pyrazinyl;
where the optionally substituted rings are optionally substituted with one or two substituents independently selected from the group consisting of fluoro, chloro, $(C_1-C_6)$alkyl, $(C_1-C_6)$alkoxy, $(C_1-C_4)$perfluoroalkyl, $(C_1-C_4)$perfluoroalkoxy, and optionally substituted phenyl;
where the optionally substituted phenyl is optionally substituted with one or two substituents independently selected from the group consisting of fluoro, chloro, $(C_1-C_6)$alkyl, $(C_1-C_6)$alkoxy, $(C_1-C_4)$perfluoroalkyl, $(C_1-C_4)$perfluoroalkoxy;
$R^2$ is hydrogen, fluoro, chloro, $(C_1-C_6)$alkyl, $(C_1-C_6)$alkoxy, $(C_1-C_4)$perfluoroalkyl, $(C_1-C_4)$perfluoroalkoxy, $(C_1-C_6)$alkylthio, $(C_1-C_6)$alkylsulfinyl, phenylsulfinyl, $(C_1-C_6)$alkylsulfonyl or phenylsulfonyl;
with the proviso that:
when $R^4$ is hydrogen then $R^5$ is $—CH(OH)X^{10}$.

2. A compound according to claim 1 or a pharmaceutically acceptable salt thereof wherein $A^2$ is

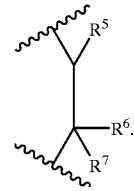

3. A compound according to claim 1 or a pharmaceutically acceptable salt thereof wherein $A^1$ is $CH_2$.

4. A compound according to claim 2 or a pharmaceutically acceptable salt thereof wherein $R^1$ is $—(CH_2)_mCX^3X^4X^5$ or a substituted five or six membered aromatic ring substituted with one substituent selected from the group consisting of carboxy, tetrazolyl, $—CO—N(H)(SO_2—X^7)$, $—N(H)(SO_2—X^7)$, $—N(H)(CO—X^7)$, and $—N(H)(CO—O$ lower alkyl) and with one or two substituents each independently selected from the group consisting of fluoro, chloro, $(C_1-C_6)$alkyl, $(C_1-C_6)$alkoxy, $(C_1-C_4)$perfluoroalkyl, and $(C_1-C_4)$perfluoroalkoxy.

5. A compound according to claim 3 or a pharmaceutically acceptable salt thereof wherein $R^1$ is a substituted phenyl substituted with one substituent selected from the group consisting of carboxy, $—N(H)(SO_2—X^7)$, $—N(H)(CO—X^7)$, and $—N(H)(CO—O$ lower alkyl) and with one or two substituents each independently selected from the group consisting of fluoro, chloro, $(C_1-C_6)$alkyl, $(C_1-C_6)$alkoxy, $(C_1-C_4)$perfluoroalkyl, and $(C_1-C_4)$perfluoroalkoxy.

6. A compound according to claim 4 or a pharmaceutically acceptable salt thereof wherein $R^4$ is hydroxy.

7. A compound according to claim 5 or a pharmaceutically acceptable salt thereof wherein $R^1$ is a substituted phenyl substituted with one substituent selected from the group consisting of carboxy, and $—N(H)(SO_2—X^7)$, and with one or two substituents each independently selected from the group consisting of fluoro, chloro, $(C_1-C_6)$alkyl, $(C_1-C_6)$alkoxy, $(C_1-C_4)$perfluoroalkyl, and $(C_1-C_4)$perfluoroalkoxy.

8. A compound according to claim 6 or a pharmaceutically acceptable salt thereof wherein n is 1; and $X^{10}$ is phenyl or phenyl substituted at the para position with phenyl.

9. A compound according to claim 7 or a pharmaceutically acceptable salt thereof wherein $R^1$ is a substituted phenyl substituted with one substituent selected from the group consisting of carboxy, and —N(H)(SO$_2$—X$^7$), and with one or two substituents each independently selected from the group consisting of fluoro, chloro and $(C_1-C_4)$perfluoroalkyl.

10. A pharmaceutical composition for the treatment of LTB$_4$ induced illnesses which comprises an effective amount of a compound according to claim 1 or a pharmaceutically acceptable salt thereof and a pharmaceutically acceptable carrier or diluent.

11. A pharmaceutical composition for the treatment of anti-inflammatory disorders, eczema, erythema, pruritus, acne, stroke, graft rejection, autoimmune diseases, or asthma, which comprises an effective amount of a compound according to claim 1 or a pharmaceutically acceptable salt thereof and a pharmaceutically acceptable carrier or diluent.

12. A method for the receptor binding inhibition of LTB$_4$ which comprises administering to a mammal in need of such inhibition an effective amount of a compound according to claim 1 or a pharmaceutically acceptable salt thereof.

13. A method for the treatment of inflammatory disorders, eczema, erythema, pruritus, acne, stroke, graft rejection, autoimmune diseases, or asthma, which comprises administering to a mammal in need of such treatment an effective amount of a compound according to claim 1 or a pharmaceutically acceptable salt thereof.

* * * * *